(12) United States Patent
Malecha

(10) Patent No.: US 9,243,276 B2
(45) Date of Patent: Jan. 26, 2016

(54) METHOD AND SYSTEM TO DETERMINE HEMATOCRIT-INSENSITIVE GLUCOSE VALUES IN A FLUID SAMPLE

(71) Applicant: LifeScan Scotland Limited, Inverness-shire (GB)

(72) Inventor: Michael Malecha, Muir of Ord (GB)

(73) Assignee: LifeScan Scotland Limited, Inverness (GB)

( * ) Notice: Subject to any disclaimer, the term of this patent is extended or adjusted under 35 U.S.C. 154(b) by 323 days.

(21) Appl. No.: 14/013,638

(22) Filed: Aug. 29, 2013

(65) Prior Publication Data

US 2015/0060302 A1    Mar. 5, 2015

(51) Int. Cl.
*G01N 27/327* (2006.01)
*C12Q 1/00* (2006.01)

(52) U.S. Cl.
CPC ............ *C12Q 1/006* (2013.01); *G01N 27/3274* (2013.01)

(58) Field of Classification Search
CPC .......... A61B 5/05; A61B 5/145; G01N 27/48; G01N 27/327; G01N 33/49; G01N 33/80; G01N 33/26; C12Q 1/00; C12Q 1/02; C12Q 1/34; C12Q 1/54
See application file for complete search history.

(56) References Cited

U.S. PATENT DOCUMENTS

| 4,919,770 | A | 4/1990 | Preidel et al. |
| --- | --- | --- | --- |
| 5,001,048 | A | 3/1991 | Taylor et al. |
| 5,243,516 | A | 9/1993 | White |
| 5,429,735 | A | 7/1995 | Johnson et al. |
| 5,437,999 | A | 8/1995 | Diebold et al. |
| 5,508,203 | A | 4/1996 | Fuller et al. |
| 5,704,354 | A | 1/1998 | Preidel et al. |
| 5,708,247 | A | 1/1998 | McAleer et al. |
| 5,792,668 | A | 8/1998 | Fuller et al. |
| 5,951,836 | A | 9/1999 | McAleer et al. |
| 6,001,239 | A | 12/1999 | Douglas et al. |
| 6,179,979 | B1 | 1/2001 | Hodges et al. |
| 6,193,873 | B1 | 2/2001 | Ohara et al. |
| 6,241,862 | B1 | 6/2001 | McAleer et al. |
| 6,284,125 | B1 | 9/2001 | Hodges et al. |
| 6,287,451 | B1 | 9/2001 | Winarta et al. |
| 6,391,645 | B1 | 5/2002 | Huang et al. |
| 6,413,410 | B1 | 7/2002 | Hodges et al. |
| 6,475,372 | B1 | 11/2002 | Ohara et al. |
| 6,517,482 | B1 | 2/2003 | Elden et al. |
| 6,576,117 | B1 | 6/2003 | Iketaki et al. |
| 6,645,368 | B1 | 11/2003 | Beaty et al. |
| 6,685,633 | B2 | 2/2004 | Albert et al. |

(Continued)

FOREIGN PATENT DOCUMENTS

| AU | 738325 B2 | 9/2001 |
| --- | --- | --- |
| EP | 749332 B1 | 3/1995 |

(Continued)

OTHER PUBLICATIONS

U.S. Appl. No. 61/530,795, filed Sep. 2, 2011, McColl et al.

(Continued)

*Primary Examiner* — Jennifer Dieterle

(57) ABSTRACT

Various embodiments of a technique to sample output signals at different time intervals from each of the electrodes in a biosensor to obtain respective glucose estimates including one where the output signals of at least one combination of electrodes measured at various time intervals are summed together to provide for a combined glucose estimate.

10 Claims, 13 Drawing Sheets

(56) References Cited

U.S. PATENT DOCUMENTS

| | | |
|---|---|---|
| 6,716,577 B1 | 4/2004 | Yu et al. |
| 6,733,655 B1 | 5/2004 | Davies et al. |
| 6,749,887 B1 | 6/2004 | Dick et al. |
| 6,767,441 B1 | 7/2004 | Cai et al. |
| 6,841,389 B2 | 1/2005 | Novikov et al. |
| 6,863,801 B2 | 3/2005 | Hodges et al. |
| 6,890,421 B2 | 5/2005 | Ohara et al. |
| 7,018,843 B2 | 3/2006 | Heller |
| 7,045,046 B2 | 5/2006 | Chambers et al. |
| 7,050,847 B2 | 5/2006 | Ollmar et al. |
| 7,258,769 B2 | 8/2007 | Cui et al. |
| 7,291,256 B2 | 11/2007 | Teodorczyk et al. |
| 7,338,639 B2 | 3/2008 | Burke et al. |
| 7,390,667 B2 | 6/2008 | Burke et al. |
| 7,407,811 B2 | 8/2008 | Burke et al. |
| 7,452,457 B2 | 11/2008 | Burke et al. |
| 7,488,601 B2 | 2/2009 | Burke et al. |
| 7,494,816 B2 | 2/2009 | Burke et al. |
| 7,498,132 B2 | 3/2009 | Yu et al. |
| 7,597,793 B2 | 10/2009 | Burke et al. |
| 7,601,249 B2 | 10/2009 | Iyengar et al. |
| 7,604,721 B2 | 10/2009 | Groll et al. |
| 7,645,373 B2 | 1/2010 | Groll et al. |
| 7,645,421 B2 | 1/2010 | Groll |
| 7,678,250 B2 | 3/2010 | Bell et al. |
| 7,718,439 B2 | 5/2010 | Groll |
| 7,727,467 B2 | 6/2010 | Burke et al. |
| 7,749,437 B2 | 7/2010 | Mosoiu et al. |
| 7,751,864 B2 | 7/2010 | Buck, Jr. |
| 7,829,023 B2 | 11/2010 | Burke et al. |
| 7,879,618 B2 | 2/2011 | Mosoiu et al. |
| 7,892,849 B2 | 2/2011 | Burke et al. |
| 7,923,258 B2 | 4/2011 | Heller |
| 7,927,882 B2 | 4/2011 | Heller |
| 7,955,492 B2 | 6/2011 | Fujiwara et al. |
| 7,964,089 B2 | 6/2011 | Harding et al. |
| 7,972,851 B2 | 7/2011 | Wang et al. |
| 7,972,861 B2 | 7/2011 | Deng et al. |
| 8,080,153 B2 | 12/2011 | Feldman et al. |
| 8,083,925 B2 | 12/2011 | Feldman et al. |
| 8,088,271 B2 | 1/2012 | Fujiwara et al. |
| 8,148,164 B2 | 4/2012 | Diebold et al. |
| 8,409,424 B2 | 4/2013 | Chen et al. |
| 8,623,660 B2 | 1/2014 | Kraft et al. |
| 2004/0005716 A9 | 1/2004 | Beaty et al. |
| 2004/0079652 A1 | 4/2004 | Vreeke et al. |
| 2004/0157339 A1 | 8/2004 | Burke et al. |
| 2007/0084734 A1 | 4/2007 | Roberts et al. |
| 2007/0087397 A1 | 4/2007 | Kraft et al. |
| 2008/0083618 A1 | 4/2008 | Neel et al. |
| 2008/0274447 A1 | 11/2008 | Mecklenburg |
| 2009/0177406 A1 | 7/2009 | Wu |
| 2009/0194432 A1 | 8/2009 | Deng |
| 2009/0223834 A1 | 9/2009 | Cai et al. |
| 2009/0236237 A1 | 9/2009 | Shinno et al. |
| 2010/0005865 A1 | 1/2010 | Miura |
| 2010/0089775 A1 | 4/2010 | Chen et al. |
| 2010/0170807 A1 | 7/2010 | Diebold et al. |
| 2010/0206749 A1 | 8/2010 | Choi |
| 2010/0276303 A1 | 11/2010 | Fujiwara et al. |
| 2010/0283488 A1 | 11/2010 | Nakamura et al. |
| 2010/0320097 A1 | 12/2010 | Miyazaki et al. |
| 2011/0030093 A1 | 2/2011 | Dhugga |
| 2011/0036729 A1 | 2/2011 | Matsuda et al. |
| 2011/0168575 A1 | 7/2011 | Lica et al. |
| 2011/0294554 A1 | 12/2011 | Barratt et al. |
| 2011/0297554 A1 | 12/2011 | Wu et al. |
| 2011/0297557 A1 | 12/2011 | Wu et al. |
| 2011/0301857 A1 | 12/2011 | Huang et al. |
| 2012/0031777 A1 | 2/2012 | Burke et al. |
| 2012/0043227 A1 | 2/2012 | Miyazaki et al. |
| 2012/0129423 A1 | 5/2012 | Finizza |

FOREIGN PATENT DOCUMENTS

| | | |
|---|---|---|
| EP | 691539 B1 | 6/1995 |
| EP | 1394545 A1 | 3/2004 |
| EP | 1828759 B1 | 10/2005 |
| EP | 1804048 B1 | 12/2005 |
| EP | 1042667 B1 | 6/2009 |
| WO | WO 9932881 A1 | 7/1999 |
| WO | WO 2006040200 A1 | 4/2006 |
| WO | WO 2006/070200 A1 | 7/2006 |
| WO | WO 2008/036516 A1 | 3/2008 |
| WO | WO 2008/040998 A2 | 4/2008 |
| WO | WO 2008/049075 A2 | 4/2008 |
| WO | WO 2010/049669 A1 | 5/2010 |
| WO | WO 2011/121292 A1 | 10/2011 |

OTHER PUBLICATIONS

U.S. Appl. No. 61/530,808, filed Sep. 2, 2011, McColl et al.
U.S. Appl. No. 61/581,087, filed Dec. 29, 2011, Malecha et al.
U.S. Appl. No. 61/581,089, filed Dec. 29, 2011, Malecha et al.
U.S. Appl. No. 61/581,099, filed Dec. 29, 2011, Malecha et al.
U.S. Appl. No. 61/581,100, filed Dec. 29, 2011, Smith et al.
U.S. Appl. No. 61/654,013, filed May 31, 2012, Malecha et al.
International Application No. PCT/GB2012/053276, PCT International Search Report and Written Opinion, 13 pages, dated May 3, 2013.
International Application No. PCT/GB2012/053277, PCT International Search Report and Written Opinion, 13 pages, dated May 3, 2013.
International Application No. PCT/GB2012/053279, PCT International Search Report and Written Opinion, 13 pages, dated May 3, 2013.
Patent Examination Report issued in related Australian Patent Application No. 2012327229, May 28, 2014, 5 pages.
Wegener, Joachim et al., "Electric Cell—Substrate Impedance Sensing (ECIS) as a Noninvasive Means to Monitor the Kinetics of Cell Spreading to Artificial Surfaces," Experimental Cell Research 259, 158-166 (2000) doi:10.1006/excr.2000.4919, available online at http://www.idealibrary.coml.
Kohma, Takuya et al., "Utilization of AC Impedance Measurements for Electrochemical Glucose Sensing Using Glucose Oxidase to Improve Detection Selectivity," Bull. Chem. Soc. Jpn. vol. 80, No. 1, 158-165 (2007).
Baskurt, Oguz K. et al., "Blood Rheology and Hemodynamics," Seminars in Thrombosis and Hemostasis, vol. 29, No. 5, 2003.
Nordbotten, Bernt, J. et al., "Methods for calculating phase angle from measured whole body bioimpedance modulus.".
Wang, J. et al., "Electrochemical Impedance Biosensor for Glucose Detection Utilizing a Periplasmic E. coli Receptor Protein," Electrochemical and Solid-State Letters, 8 (8) H61-H64 (2005).
Caduff, A. et al., "First human experiments with a novel non-invasive, non-optical continuous glucose monitoring system," Biosensors and Bioelectronics 19 (2003) 209-217.
Guevara, Edgar et al., "Prediction of Glucose Concentration by Impedance Phase Measurements," CP1032, Medical Physics—Tenth Symposium of Medical Physics, 2008 American Institute of Physics 978-0-7354-0556, 259-261.
Park, J.-H. et al., "The correlation of the complex dielectric constant and blood glucose at low frequency," Biosensors and Bioelectronics 19 (2003) 321-324.
De Vries, P.M.J.M. et al., "Implications of the dielectrical behavior of human blood for continuous online measurement of haematocrit," Med. & Biol. Eng. & Comput. 1993, 31, 445-448.
"Annex A—Bioimpedance monitoring for physicians: an overview," pp. 131-178.
Koschinsky, T. et al., "Sensors for glucose monitoring: technical and clinical aspects," Diabetes Metab Res Rev 2001; 17: 113-123.
Marks, Vincent, "Blood glucose: its measurement and clinical importance," Clinica Chimica Acta 251 (1996) 3-17.
Shervedani, Reza Karimi et al., "A novel method for glucose determination based on electrochemical impedance spectroscopy using glucose oxidase self-assembled biosensor," Bioelectrochemistry 69 (2006) 201-208.

(56) References Cited

OTHER PUBLICATIONS

Tura, Andrea et al., "Non-invasive glucose monitoring: Assessment of technologies and devices according to quantitative criteria," Diabetes Research and Clinical Practice 77 (2007) 16-40.

Tierney, M.J. et al., "Clinical evaluation of the GlucoWatch® biographer: a continual, non-invasive glucose monitor for patients with diabetes," Biosensors & Bioelectronics 16 (2001) 621-629.

Tura, A. et al., "Impedance spectroscopy of solutions at physiological glucose concentrations," Biophysical Chemistry 129 (2007) 235-241.

International Preliminary Report on Patentability issued in related International Patent Application No. PCT/GB2012/053279, issued Jul. 1, 2004, 10 pages.

Patent Examination Report issued in related Australian Patent Application No. 2012340500, issued Aug. 4, 2014, 3 pages.

International Preliminary Report on Patentability issued in related International Patent Application No. PCT/GB2012/053277, issued Jul. 1, 2004, 11 pages.

International Preliminary Report on Patentability issued in related International Patent Application No. PCT/GB2012/053276, issued Jul. 1, 2004, 11 pages.

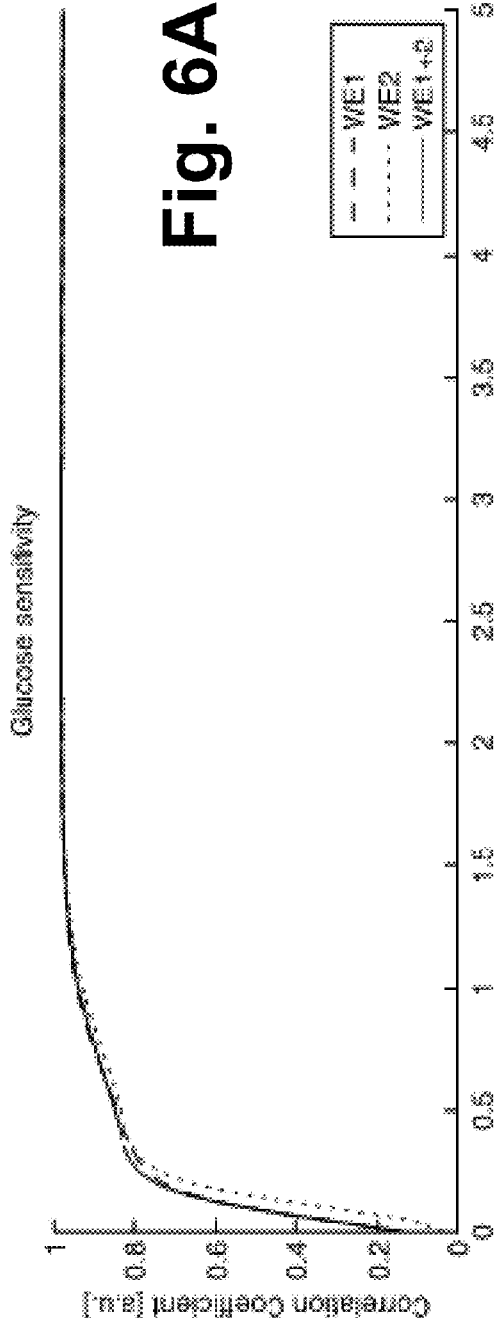
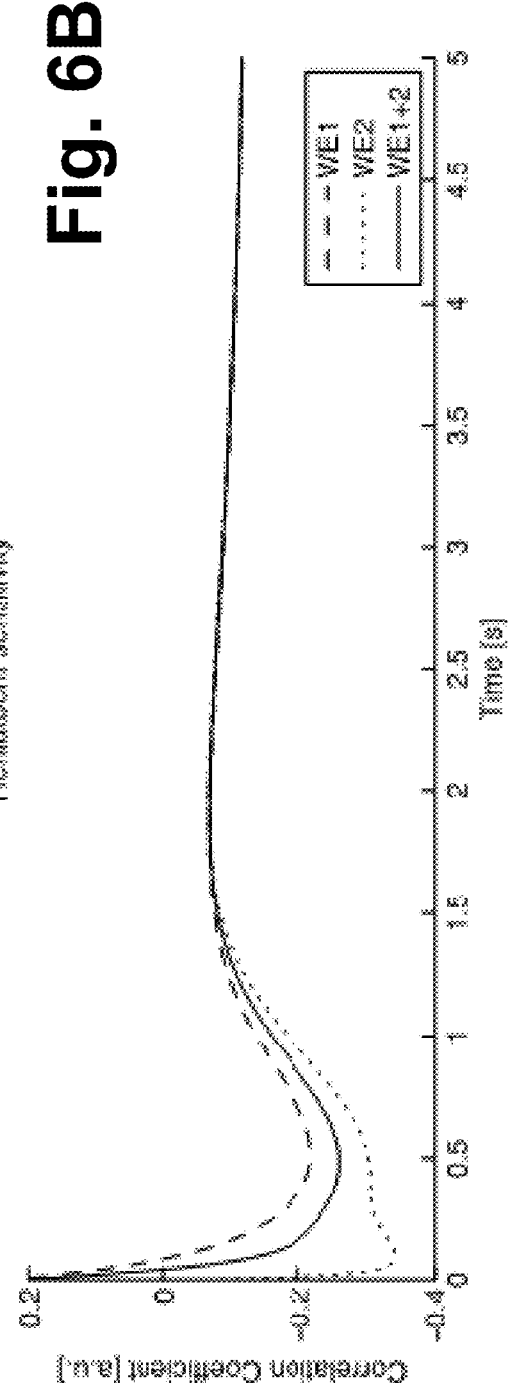

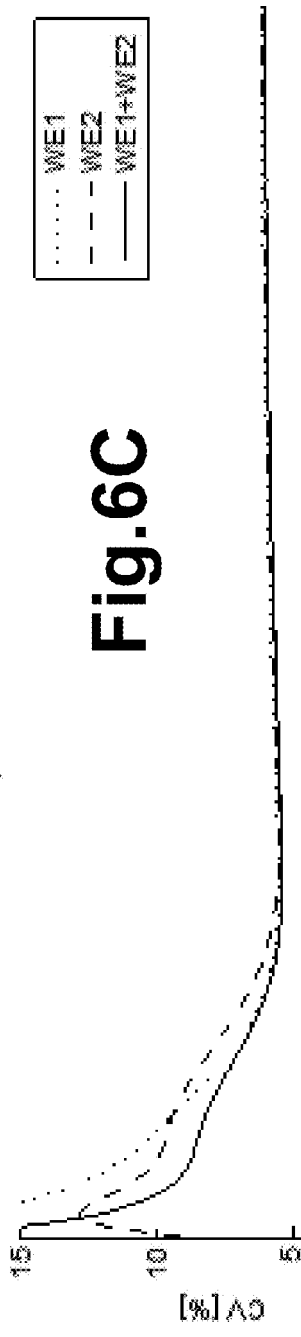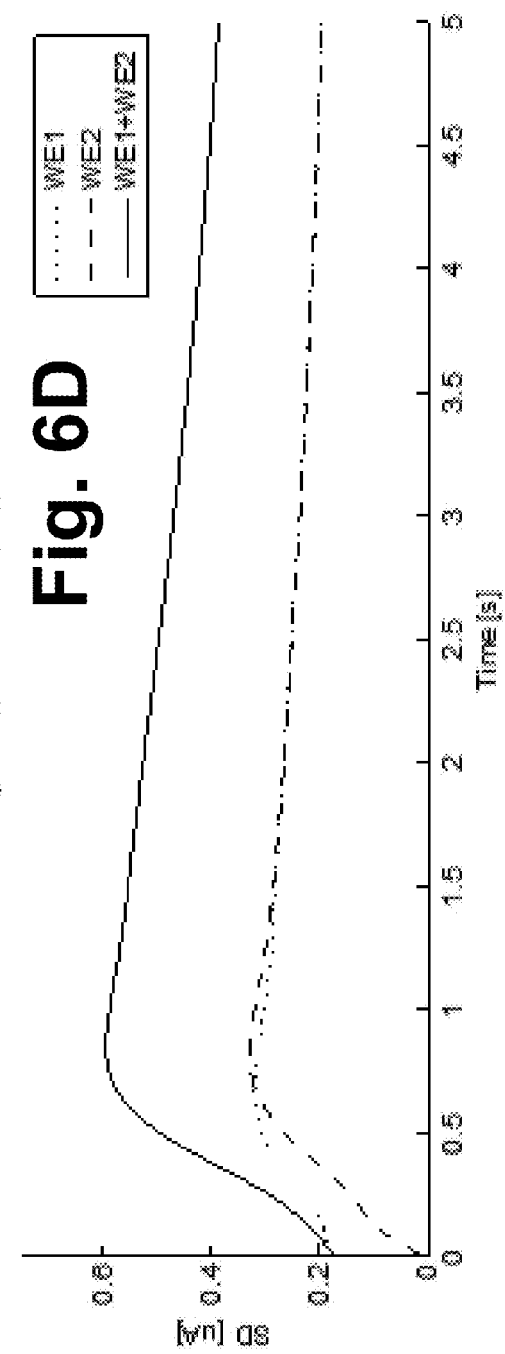

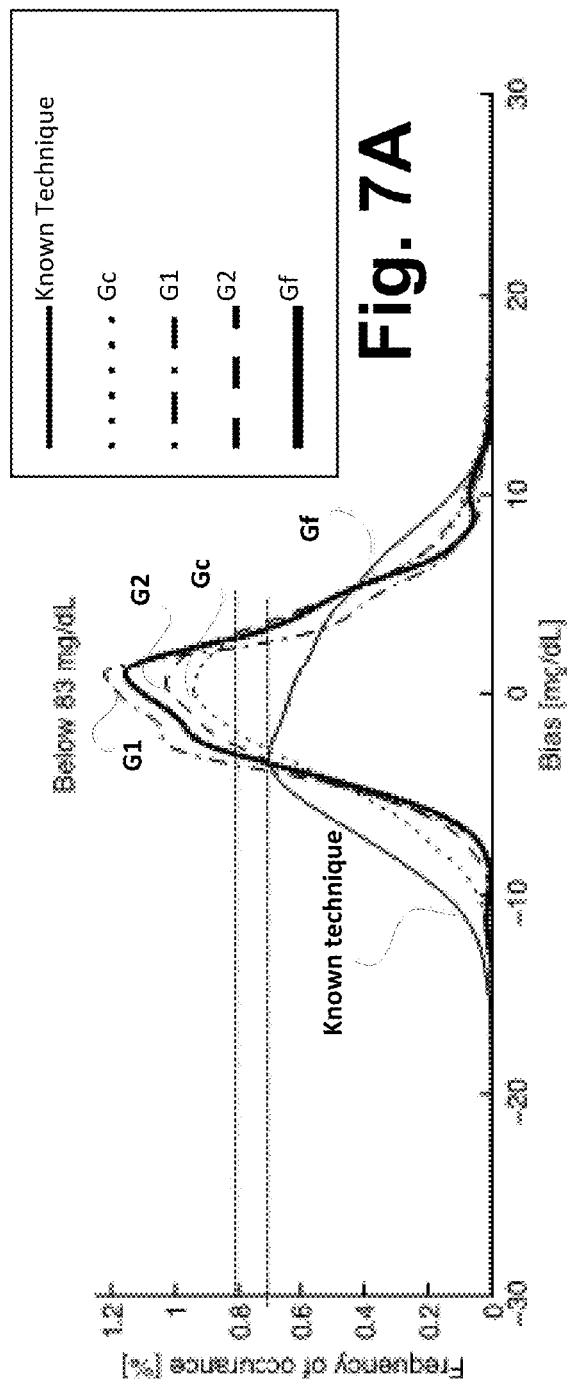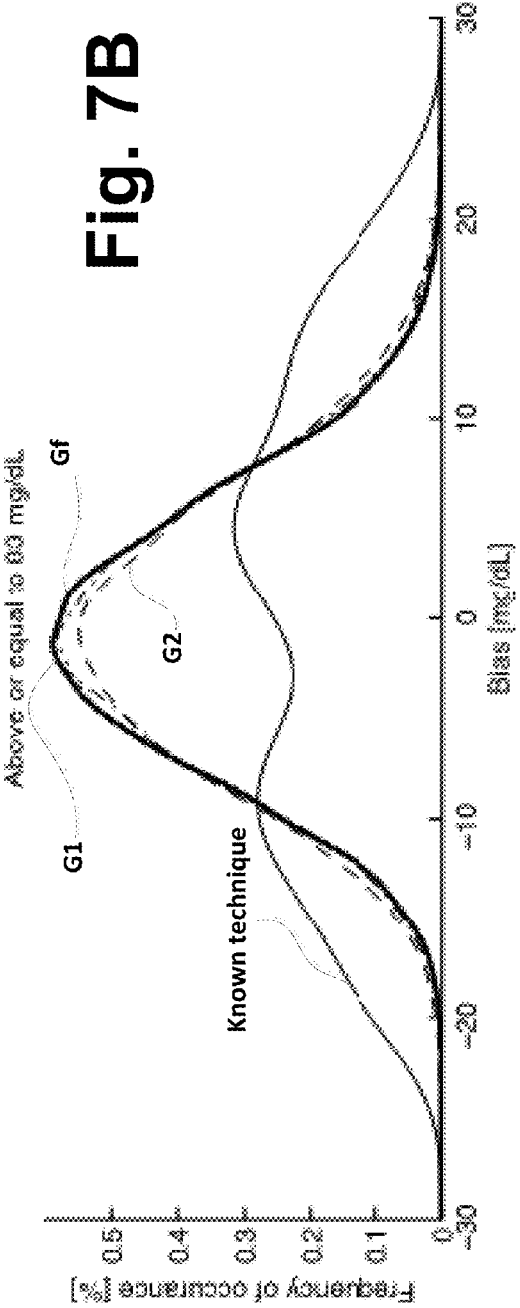

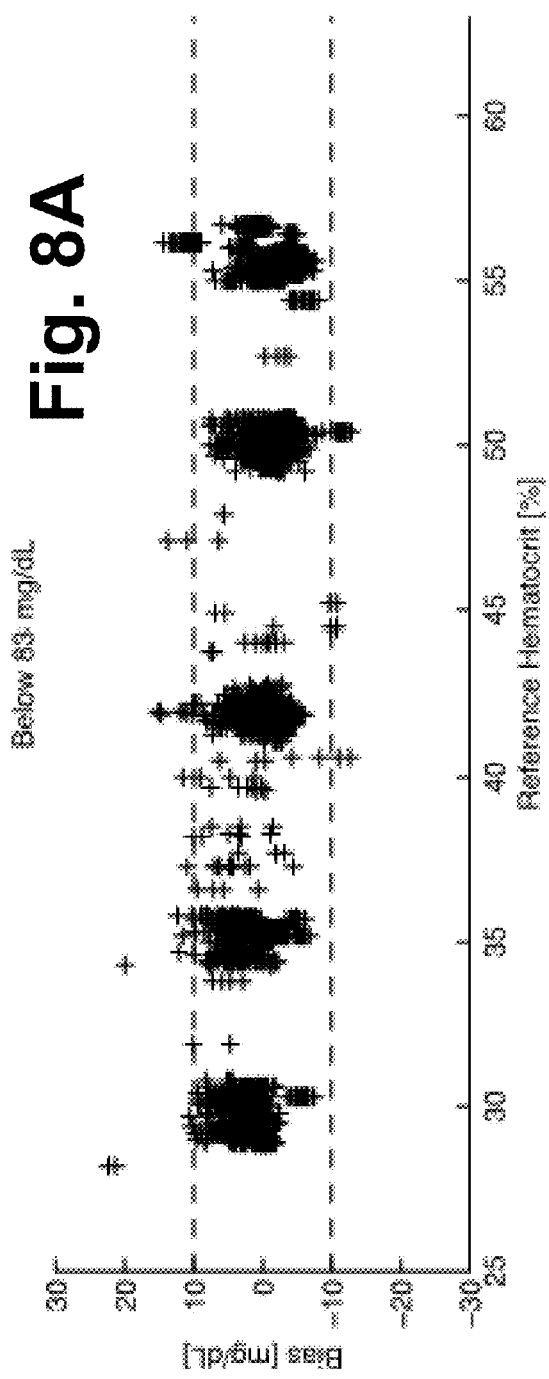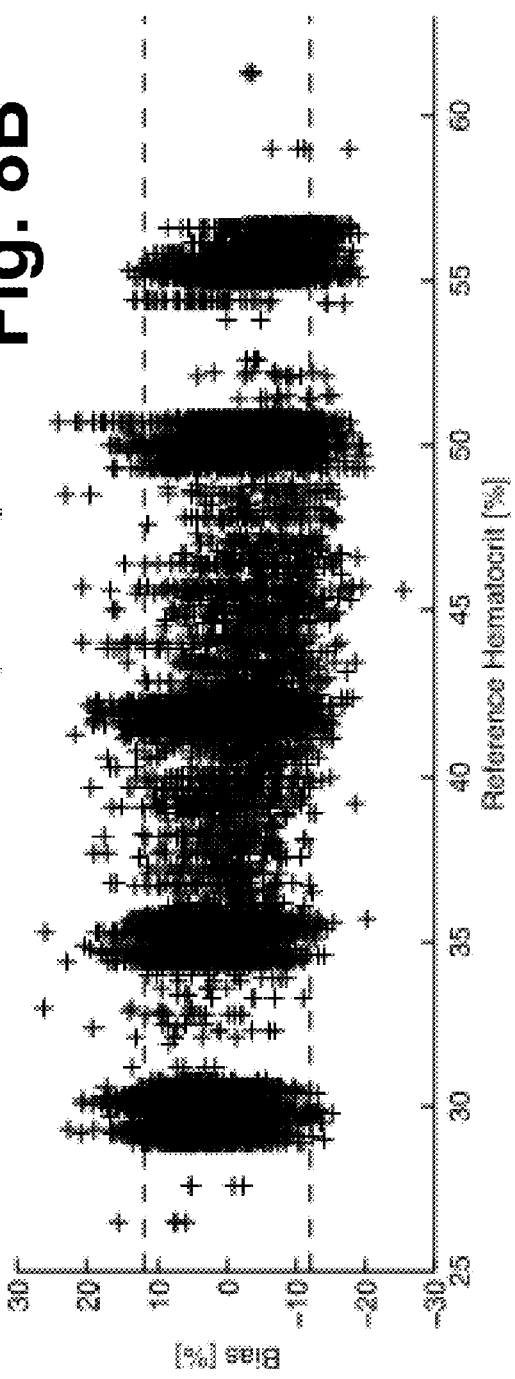

METHOD AND SYSTEM TO DETERMINE HEMATOCRIT-INSENSITIVE GLUCOSE VALUES IN A FLUID SAMPLE

BACKGROUND

Electrochemical glucose test strips, such as those used in the OneTouch® Ultra® whole blood testing kit, which is available from LifeScan, Inc., are designed to measure the concentration of glucose in a blood sample from patients with diabetes. The measurement of glucose can be based on the selective oxidation of glucose by the enzyme glucose oxidase (GO). The reactions that can occur in a glucose test strip are summarized below in Equations 1 and 2.

$$\text{Glucose} + GO_{(ox)} \rightarrow \text{Gluconic Acid} + GO_{(red)} \quad \text{Eq. 1}$$

$$GO_{(red)} + 2Fe(CN)_6^{3-} \rightarrow GO_{(ox)} + 2Fe(CN)_6^{4-} \quad \text{Eq. 2}$$

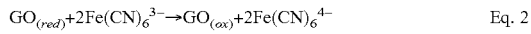

As illustrated in Equation 1, glucose is oxidized to gluconic acid by the oxidized form of glucose oxidase ($GO_{(ox)}$). It should be noted that $GO_{(ox)}$ may also be referred to as an "oxidized enzyme." During the reaction in Equation 1, the oxidized enzyme $GO_{(ox)}$ is converted to its reduced state, which is denoted as $GO_{(red)}$ (i.e., "reduced enzyme"). Next, the reduced enzyme $GO_{(red)}$ is re-oxidized back to $GO_{(ox)}$ by reaction with $Fe(CN)_6^{3-}$ oxidized (referred to as either the oxidized mediator or ferricyanide) as illustrated in Equation 2. During the re-generation of $GO_{(red)}$ back to its oxidized state $GO_{(ox)}$, $Fe(CN)_6^{3-}$ is reduced to $Fe(CN)_6^{4-}$ (referred to as either reduced mediator or ferrocyanide).

When the reactions set forth above are conducted with a test voltage applied between two electrodes, a test output signal can be created by the electrochemical re-oxidation of the reduced mediator at the electrode surface. Thus, since, in an ideal environment, the amount of ferrocyanide created during the chemical reaction described above is directly proportional to the amount of glucose in the sample positioned between the electrodes, the test output signal generated would be proportional to the glucose content of the sample. A mediator, such as ferricyanide, is a compound that accepts electrons from an enzyme such as glucose oxidase and then donates the electrons to an electrode. As the concentration of glucose in the sample increases, the amount of reduced mediator formed also increases; hence, there is a direct relationship between the test output signal, resulting from the re-oxidation of reduced mediator, and glucose concentration. In particular, the transfer of electrons across the electrical interface results in the flow of a test output signal (2 moles of electrons for every mole of glucose that is oxidized). The test output signal resulting from the introduction of glucose can, therefore, be referred to as a glucose output signal.

Because it can be very important to know the concentration of glucose in blood, particularly in people with diabetes, test meters have been developed using the principals set forth above to enable the average person to sample and test their blood for determining their glucose concentration at any given time. The glucose output signal generated is detected by the test meter and converted into a glucose concentration reading using an algorithm that relates the test output signal to a glucose concentration via a simple mathematical formula. In general, the test meters work in conjunction with a disposable test strip that may include a sample-receiving chamber and at least two electrodes disposed within the sample-receiving chamber in addition to the enzyme (e.g. glucose oxidase) and the mediator (e.g. ferricyanide). In use, the user pricks their finger or other convenient site to induce bleeding and introduces a blood sample to the sample-receiving chamber, thus starting the chemical reaction set forth above.

SUMMARY OF THE DISCLOSURE

In one aspect, applicant has devised a glucose measurement system that includes a biosensor and a meter. The biosensor has a plurality of electrodes with a reagent disposed thereon. The meter includes a microcontroller coupled to a power source, memory and the plurality of electrodes of the biosensor. The microcontroller is configured to: apply a signal to the at least two electrodes after application of a fluid sample proximate the at least two electrodes to start a test measurement sequence for an electrochemical reaction of the glucose in the fluid sample with the enzyme; obtain an estimate representative of the glucose in the fluid sample from respective output signals of each of the plurality of the electrodes at a plurality of selected time intervals from the start of the test measurement sequence; obtain another estimate representative of the glucose in the fluid sample from a combination of respective output signals from the plurality of electrodes at a plurality of specific time intervals from the start of the test measurement sequence; and determine a final glucose value of the fluid sample from a median of all the estimates of the glucose in the fluid sample.

In a second aspect, a method of determining a glucose value from a fluid sample with a biosensor and a glucose meter is provided. The biosensor has at least two electrodes and reagent disposed thereon. The glucose meter has a microcontroller configured to connect to the biosensor and to a memory and a power source. The method can be achieved by: initiating a start of a test measurement sequence upon deposition of a fluid sample proximate the at least two electrodes of the biosensor; applying an input signal to the plurality of electrodes with the fluid sample to cause a transformation of glucose into an enzymatic by-product; determining a plurality of glucose concentration estimates from the plurality output signal transients from the plurality of electrodes and the fluid sample; and deriving a final glucose concentration from a median of all of the plurality of glucose concentration estimates.

And for these aspects, the following features may also be utilized in various combinations with these previously disclosed aspects: the microcontroller obtains a glucose estimate from the output signal of one electrode out of the plurality of electrodes at about 1.5 seconds, 1 seconds, 1.7 seconds, 1.2 seconds, and 0.7 seconds from the start of the test measurement sequence; the microcontroller obtains a glucose estimate from the output signal of another electrode out of the plurality of electrodes at about 4.4 seconds, 1.2 seconds, 2.5 seconds, 3.7 seconds, and 3.4 seconds from the start of the test measurement sequence; the microcontroller obtains a glucose estimate from a summation of the respective output signals of two electrodes of the plurality of electrodes at about 2.5 seconds, 0.7 seconds, 1.5 seconds, 1.2 seconds and 0.5 seconds from the start of the test measurement sequence; the glucose estimate of the one electrode is obtained with an equation of the form:

$$G_1 = \left( \left( \frac{I_{r1}}{I_{r2}} \right)^{x_1} \times \frac{x_2 I_{r3}^3 + x_3 I_{r3}^2 + x_4 I_{r3} + x_5}{x_5 I_{r6}^3 + x_7 I_{r4}^2 + x_8 I_{r4} + x_9} \times x_{10} I_{r5} - x_{11} \right) / x_{12}$$

Where G1 may include a first glucose estimate;
$I_{r1}$ may be an output signal sampled at a time interval at about 1.5 seconds from the start of the test sequence;

$I_{t2}$ may include an output signal sampled at a time interval at about 1 second from the start of the test sequence;

$I_{t3}$ may include an output signal sampled at a time interval at about 1.7 seconds from the start of the test sequence;

$I_{t4}$ may include an output signal sampled at a time interval at about 1.2 seconds from the start of the test sequence;

$I_{t5}$ may include an output signal sampled at a time interval at about 0.7 seconds from the start of the test sequence;

$x_1$ may include a coefficient of about 1.6;

$x_2$ may include a coefficient of about 1.9E−01;

$x_3$ may include a coefficient of about −3.6E−01;

$x_4$ may include a coefficient of about 1.2E+01;

$x_5$ may include a coefficient of about 1.6;

$x_6$ may include a coefficient of about 1.7E−02;

$x_7$ may include a coefficient of about 2.1E−01;

$x_8$ may include a coefficient of about −4.0E−01;

$x_9$ may include a coefficient of about 2.4;

$x_{10}$ may include a coefficient of about 2.1;

$x_{11}$ may include a coefficient of about 4.6E−01; and $x_{12}$ may include a coefficient of about 3.9E−01;

the glucose estimate of the other electrode is obtained with an equation of the form:

$$G_2 = \left(\left(\frac{I_{t1}}{I_{t2}}\right)^{x_1} \times \frac{x_2 I_{t3}^3 + x_3 I_{t3}^2 + x_4 I_{t3} + x_5}{x_5 I_{t6}^3 + x_7 I_{t4}^2 + x_8 I_{t4} + x_9} \times x_{10} I_{t5} - x_{11}\right)/x_{12}$$

Where $G_2$ may include a second glucose estimate;

$I_{t1}$ may include an output signal sampled at a time interval at about 4.4 seconds from the start of the test sequence;

$I_{t2}$ may include an output signal sampled at a time interval at about 1.2 seconds from the start of the test sequence;

$I_{t3}$ may include an output signal sampled at a time interval at about 2.5 seconds from the start of the test sequence;

$I_{t4}$ may be an output signal sampled at a time interval at about 3.7 seconds from the start of the test sequence;

$I_{t5}$ may be an output signal sampled at a time interval at about 3.4 seconds from the start of the test sequence;

$x_1$ may include a coefficient of about 8.5E−01;

$x_2$ may include a coefficient of about 7.4E−01;

$x_3$ may include a coefficient of about −4.2;

$x_4$ may include a coefficient of about 5.7;

$x_5$ may include a coefficient of about 1.4;

$x_6$ may include a coefficient of about 5E−02;

$x_7$ may include a coefficient of about 1.3E−01;

$x_8$ may include a coefficient of about −1.5;

$x_9$ may include a coefficient of about 2.4;

$x_{10}$ may include a coefficient of about 6E−01;

$x_{11}$ may include a coefficient of about −8.6; and $x_{12}$ may include a coefficient of about 1.9E−01;

the glucose estimate of the two electrodes is obtained with an equation of the form:

$$G_c = \left(\left(\frac{I_{t1}}{I_{t2}}\right)^{x_1} \times \frac{x_2 I_{t3}^3 + x_3 I_{t3}^2 + x_4 I_{t3} + x_5}{x_5 I_{t6}^3 + x_7 I_{t4}^2 + x_8 I_{t4} + x_9} \times x_{10} I_{t5} - x_{11}\right)/x_{12}$$

Where $G_c$ may include a combined glucose estimate;

$I_{t1}$ may include a summation of output signals from the plurality of electrodes sampled at a time interval at about 2.5 seconds from the start of the test sequence;

$I_{t2}$ may include a summation of output signals from the plurality of electrodes sampled at a time interval at about 0.7 seconds from the start of the test sequence;

$I_{t3}$ may include a summation of output signals from the plurality of electrodes sampled at a time interval at about 1.5 seconds from the start of the test sequence;

$I_{t4}$ may include a summation of output signals from the plurality of electrodes sampled at a time interval at about 1.2 seconds from the start of the test sequence;

$I_{t5}$ may include a summation of output signals from the plurality of electrodes sampled at a time interval at about 0.5 seconds from the start of the test sequence;

$x_1$ may include a coefficient of about 1;

$x_2$ may include a coefficient of about 3.1;

$x_3$ may include a coefficient of about −1.9E01;

$x_4$ may include a coefficient of about 2.7E01;

$x_5$ may include a coefficient of about 9.8;

$x_6$ may include a coefficient of about 2.6;

$x_7$ may include a coefficient of about −6.5;

$x_8$ may include a coefficient of about −1.9E01; and $x_9$ may include a coefficient of about 6.7E01;

$x_{10}$ may include a coefficient of about 1.9E01;

$x_{11}$ may include a coefficient of about −2.3E01; and $x_{12}$ may include a coefficient of about 3.9E−01.

These and other embodiments, features and advantages will become apparent to those skilled in the art when taken with reference to the following more detailed description of the exemplary embodiments of the invention in conjunction with the accompanying drawings that are first briefly described.

BRIEF DESCRIPTION OF THE DRAWINGS

The accompanying drawings, which are incorporated herein and constitute part of this specification, illustrate presently preferred embodiments of the invention, and, together with the general description given above and the detailed description given below, serve to explain features of the invention (wherein like numerals represent like elements), in which:

FIG. 4A illustrates a graph of time over applied potential to the test strip of

FIG. 1 or FIG. 3C.

FIGS. 6A and 6B provide comparisons of each of the estimated glucose values G1 (measured by working electrode WE1), G2 (measured by working electrode WE2), Gc (measured by a sum of WE1 and WE2), and the final glucose value Gf.

FIGS. 6C and 6D provide a comparisons for coefficient of variations (CV) and standard deviation (SD) for each of the estimated glucose values G1 (measured by working electrode WE1), G2 (measured by working electrode WE2), Gc (measured by a sum of WE1 and WE2), and the final glucose value Gf.

FIG. 7A provides a comparison of the accuracy between the known technique, the estimated glucose values G1 (measured by working electrode WE1), G2 (measured by working electrode WE2), Gc (measured by a sum of the measured signals from WE1 and WE2), and the final glucose value Gf for measurements of referential glucose below 83 mg/dL.

FIG. 7B provides a comparison of the accuracy between the known technique, the estimated glucose values G1 (measured by working electrode WE1), G2 (measured by working electrode WE2), Gc (measured by a sum of signals from both WE1 and WE2), and the final glucose value Gf for measurements of referential glucose at or above 83 mg/dL.

FIG. 8A illustrates the "bias" or error (in terms of ±10 mg/dL) between referential and measured glucose values using my technique for referential glucose values below 83 mg/dL;

FIG. 8B illustrates the "bias" or error (in terms of ±12% error) between referential and measured glucose values using my technique for referential glucose values at or above 83 mg/dL.

MODES OF CARRYING OUT THE INVENTION

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±10% of the recited value, e.g. "about 90%" may refer to the range of values from 81% to 99%. In addition, as used herein, the terms "patient," "host," "user," and "subject" refer to any human or animal subject and are not intended to limit the systems or methods to human use, although use of the subject invention in a human patient represents a preferred embodiment. As used herein, "oscillating signal" includes voltage signal(s) or current signal(s) that, respectively, change polarity or alternate direction of current or are multi-directional. Also used herein, the phrase "electrical signal" or "signal" is intended to include direct current signal, alternating signal or any signal within the electromagnetic spectrum. The terms "processor"; "microprocessor"; or "microcontroller" are intended to have the same meaning and are intended to be used interchangeably.

Figure 1:
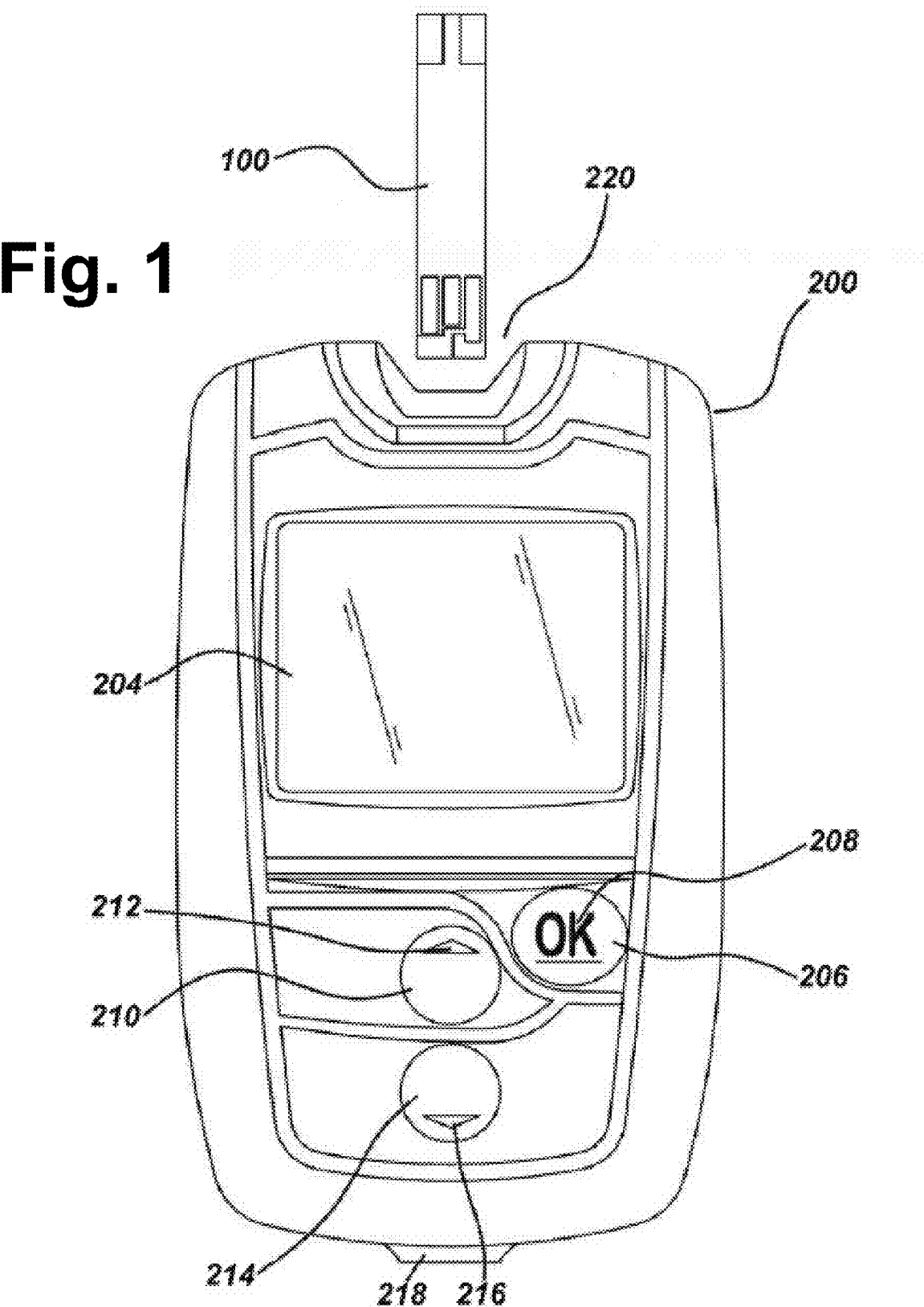
FIG. 1 illustrates a glucose measurement system.

FIG. 1 illustrates a glucose measurement system having test strip 100 and test meter 200, for testing glucose levels in the blood of an individual with methods and techniques illustrated and described herein. Test meter 200 may include user interface inputs (206, 210, 214), which can be in the form of buttons, for entry of data, navigation of menus, and execution of commands. Data can include values representative of analyte concentration, and/or information that are related to the everyday lifestyle of an individual. Information, which is related to the everyday lifestyle, can include food intake, medication use, the occurrence of health check-ups, general health condition and exercise levels of an individual. Test meter 200 can also include a display 204 that can be used to report measured glucose levels, and to facilitate entry of lifestyle related information.

Test meter 200 may include a first user interface input 206, a second user interface input 210, and a third user interface input 214. User interface inputs 206, 210, and 214 facilitate entry and analysis of data stored in the testing device, enabling a user to navigate through the user interface displayed on display 204. User interface inputs 206, 210, and 214 include a first marking 208, a second marking 212, and a third marking 216, which help in correlating user interface inputs to characters on display 204.

Test meter 200 can be turned on by inserting a test strip 100 into a strip port connector 220, by pressing and briefly holding first user interface input 206, or by the detection of data traffic across a data port 218. Test meter 200 can be switched off by removing test strip 100, pressing and briefly holding first user interface input 206, navigating to and selecting a meter off option from a main menu screen, or by not pressing any buttons for a predetermined time. Display 204 can optionally include a backlight.

In one embodiment, test meter 200 can be configured to not receive a calibration input for example, from any external source, when switching from a first test strip batch to a second test strip batch. Thus, in one exemplary embodiment, the meter is configured to not receive a calibration input from external sources, such as a user interface (such as inputs 206, 210, 214), an inserted test strip, a separate code key or a code strip, or wireless or wired code to the data port 218. Such a calibration input is not necessary when all of the test strip batches have a substantially uniform calibration characteristic. The calibration input can be a set of values ascribed to a particular test strip batch. For example, the calibration input can include a batch slope and a batch intercept value for a particular test strip batch. The calibrations input, such as batch slope and intercept values, may be preset within the meter as will be described below.

Figure 2:
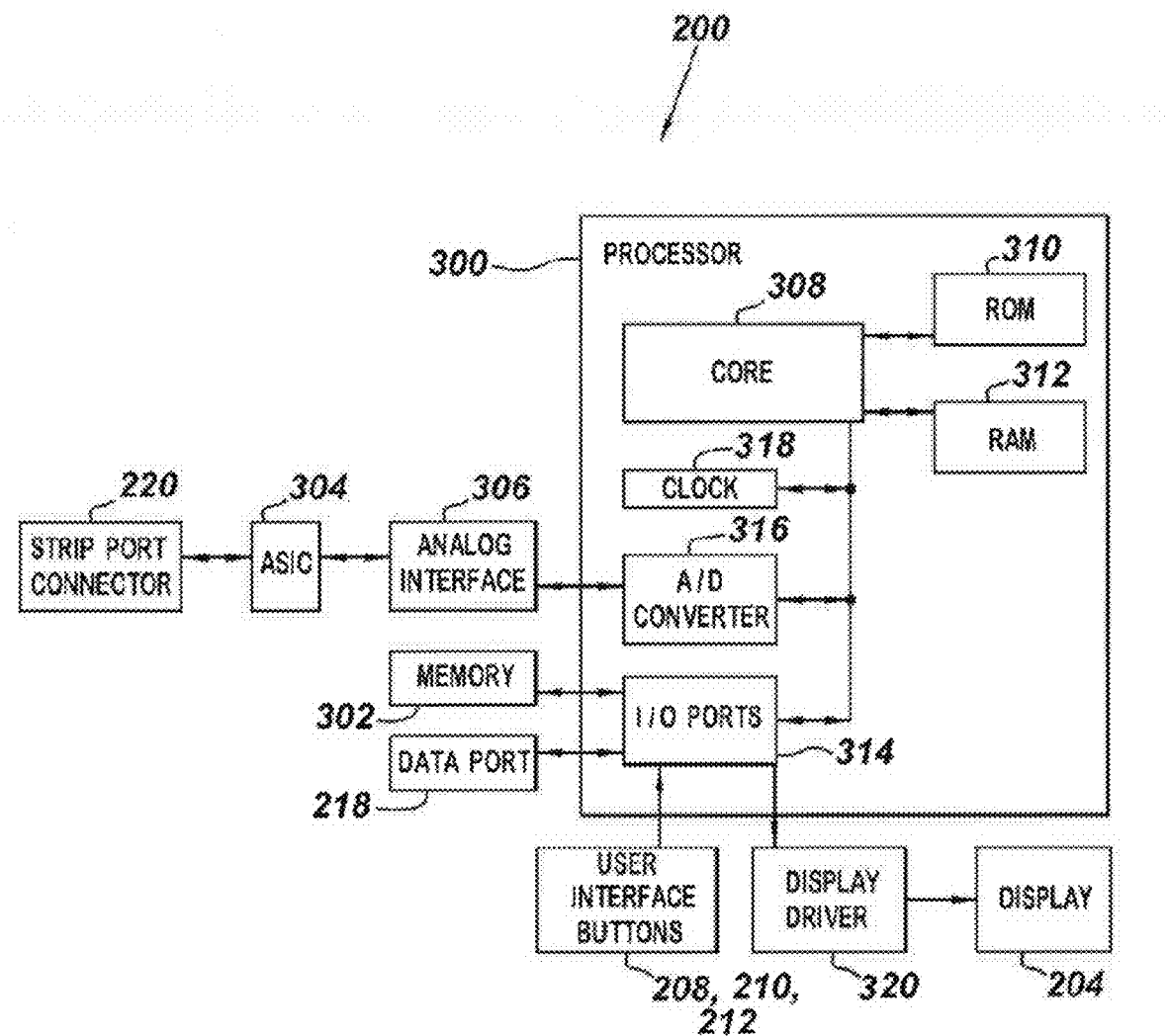
FIG. 2 illustrates in simplified schematic form the components of the meter 200.

Referring to FIG. 2, an exemplary internal layout of test meter 200 is shown. Test meter 200 may include a processor 300, which in some embodiments described and illustrated herein is a 32-bit RISC microcontroller. In the preferred embodiments described and illustrated herein, processor 300 is preferably selected from the MSP 430 family of ultra-low power microcontrollers manufactured by Texas Instruments of Dallas, Tex. The processor can be bi-directionally connected via I/O ports 314 to a memory 302, which in some embodiments described and illustrated herein is an EEPROM. Also connected to processor 300 via I/O ports 214 are the data port 218, the user interface inputs 206, 210, and 214, and a display driver 320. Data port 218 can be connected to processor 300, thereby enabling transfer of data between memory 302 and an external device, such as a personal computer. User interface inputs 208, 210, and 214 are directly connected to processor 300. Processor 300 controls display 204 via display driver 320. Memory 302 may be pre-loaded with calibration information, such as batch slope and batch intercept values, during production of test meter 200. This pre-loaded calibration information can be accessed and used by processor 300 upon receiving a suitable signal (such as current) from the strip via strip port connector 220 so as to calculate a corresponding analyte level (such as blood glucose concentration) using the signal and the calibration information without receiving calibration input from any external source.

In embodiments described and illustrated herein, test meter 200 may include an Application Specific Integrated Circuit (ASIC) 304, so as to provide electronic circuitry used in measurements of glucose level in blood that has been applied to a test strip 100 inserted into strip port connector 220. Analog voltages can pass to and from ASIC 304 by way of an analog interface 306. Analog signals from analog interface 306 can be converted to digital signals by an A/D converter 316. Processor 300 further includes a core 308, a ROM 310 (containing computer code), a RAM 312, and a clock 318. In one embodiment, the processor 300 is configured (or programmed) to disable all of the user interface inputs except for a single input upon a display of an analyte value by the display unit such as, for example, during a time period after an analyte measurement. In an alternative embodiment, the processor 300 is configured (or programmed) to ignore any input from all of the user interface inputs except for a single input upon a display of an analyte value by the display unit.

Figure 3A:
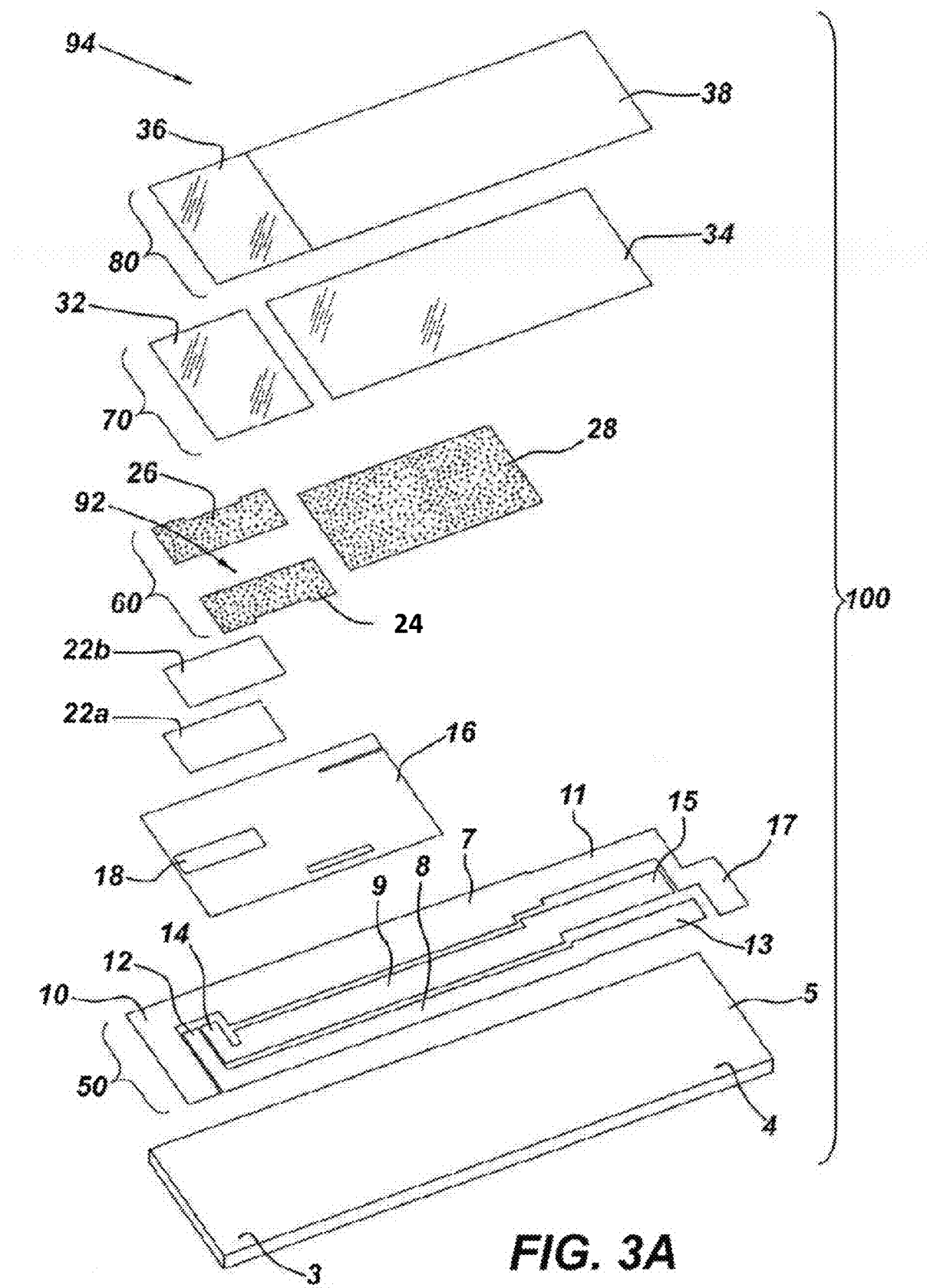
FIG. 3A illustrates the test strip 100 of the system of FIG. 1.

FIG. 3A is an exemplary exploded perspective view of a test strip 100, which may include seven layers disposed on a substrate 5. The seven layers disposed on substrate 5 can be a conductive layer 50 (which can also be referred to as electrode layer 50), an insulation layer 16, two overlapping reagent layers 22a and 22b, an adhesive layer 60 which includes adhesive portions 24, 26, and 28, a hydrophilic layer 70, and a top layer 80. Test strip 100 may be manufactured in a series of steps where the conductive layer 50, insulation layer 16, reagent layers 22, and adhesive layer 60 are sequentially deposited on substrate 5 using, for example, a screen-printing process. Hydrophilic layer 70 and top layer 80 can be disposed from a roll stock and laminated onto substrate 5 as either an integrated laminate or as separate layers. It is noted that the reagent includes both the enzymes and other materials such as binders and other materials to allow the reagent to function for its intended purpose in a biosensor. Test strip 100 has a distal portion 3 and a proximal portion 4 as shown in FIG. 3A.

Test strip 100 may include a sample-receiving chamber 92 through which a blood sample may be drawn. Sample-receiving chamber 92 can include an inlet at a proximal end and an outlet at the side edges of test strip 100, as illustrated in FIG. 3A. A blood sample 94 can be applied to the inlet to fill a sample-receiving chamber 92 so that glucose can be measured. The side edges of a first adhesive pad 24 and a second adhesive pad 26 located adjacent to reagent layer 22 each define a wall of sample-receiving chamber 92, as illustrated in FIG. 3A. A bottom portion or "floor" of sample-receiving chamber 92 may include a portion of substrate 5, conductive layer 50, and insulation layer 16, as illustrated in FIG. 3A. A top portion or "roof" of sample-receiving chamber 92 may include distal hydrophilic portion 32, as illustrated in FIG. 3A.

For test strip 100, as illustrated in FIG. 3A, substrate 5 can be used as a foundation for helping support subsequently applied layers. Substrate 5 can be in the form of a polyester sheet such as a polyethylene tetraphthalate (PET) material (Hostaphan PET supplied by Mitsubishi). Substrate 5 can be in a roll format, nominally 350 microns thick by 370 millimeters wide and approximately 60 meters in length.

A conductive layer is required for forming electrodes that can be used for the electrochemical measurement of glucose. Conductive layer 50 can be made from a carbon ink that is screen-printed onto substrate 5. In a screen-printing process, carbon ink is loaded onto a screen and then transferred through the screen using a squeegee. The printed carbon ink can be dried using hot air at about 140° C. The carbon ink can include VAGH resin, carbon black, graphite (KS15), and one or more solvents for the resin, carbon and graphite mixture. More particularly, the carbon ink may incorporate a ratio of carbon black:VAGH resin of about 2.90:1 and a ratio of graphite:carbon black of about 2.62:1 in the carbon ink.

For test strip 100, as illustrated in FIG. 3A, conductive layer 50 may include a reference electrode 10, a first working electrode 12, a second working electrode 14, a first contact pad 13, a second contact pad 15, a reference contact pad 11, a first working electrode track 8, a second working electrode track 9, a reference electrode track 7, and a strip detection bar 17. The conductive layer may be formed from carbon ink. First contact pad 13, second contact pad 15, and reference contact pad 11 may be adapted to electrically connect to a test meter. First working electrode track 8 provides an electrically continuous pathway from first working electrode 12 to first contact pad 13. Similarly, second working electrode track 9 provides an electrically continuous pathway from second working electrode 14 to second contact pad 15. Similarly, reference electrode track 7 provides an electrically continuous pathway from reference electrode 10 to reference contact pad 11. Strip detection bar 17 is electrically connected to reference contact pad 11. A test meter can detect that test strip 100 has been properly inserted by measuring a continuity between reference contact pad 11 and strip detection bar 17, as illustrated in FIG. 3A.

Figure 3B:
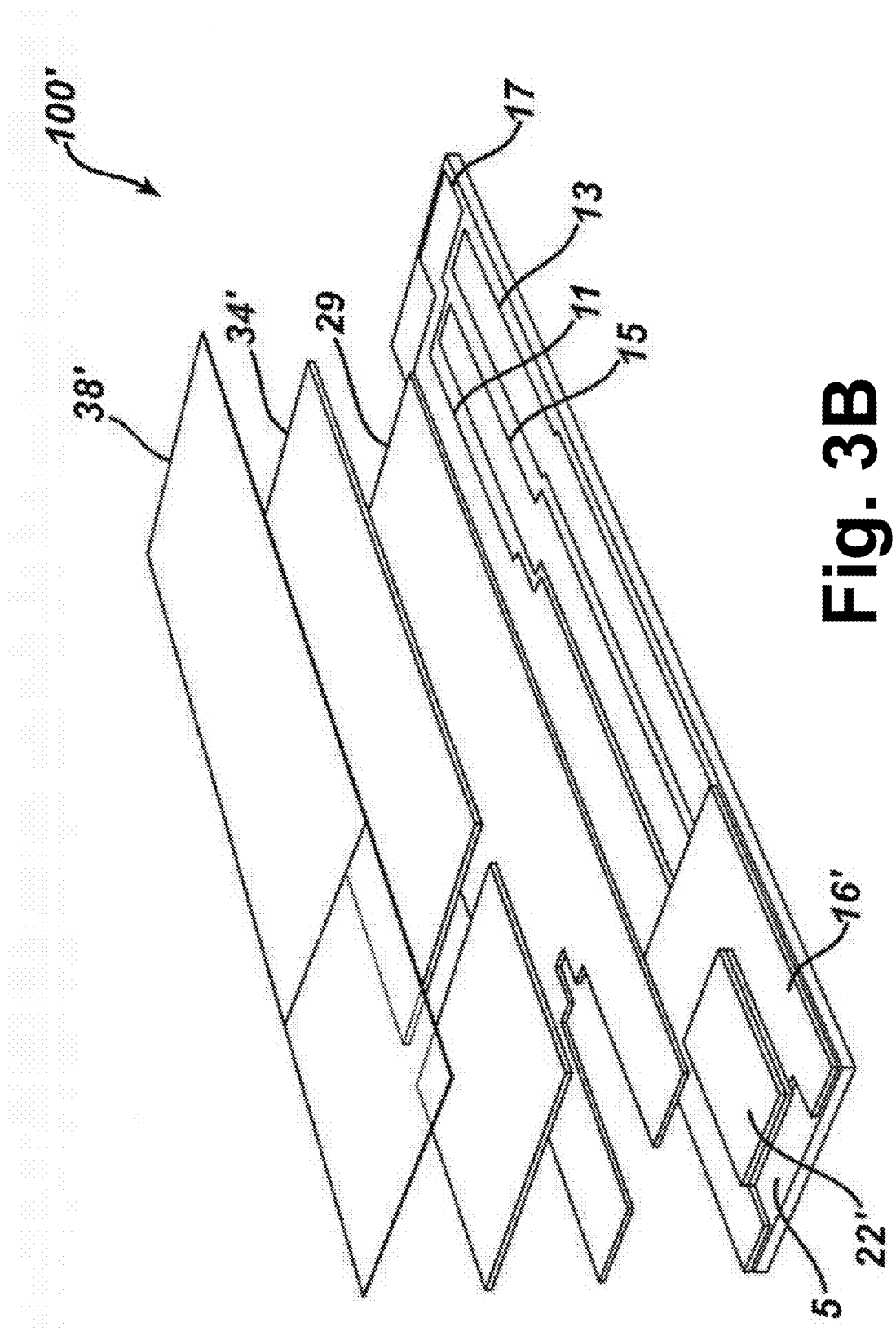
FIG. 3B illustrates in perspective view for an alternate test strip 100' for the system of FIG. 1.

An alternate version of the test strip 100 is shown in FIG. 3B as strip 100'. In this version, the top layer 38', hydrophilic film layer 34' and spacer 29 have been combined together to form an integrated assembly for mounting to the substrate 5 with reagent layer 22' disposed proximate insulation layer 16'.

Figure 3C:
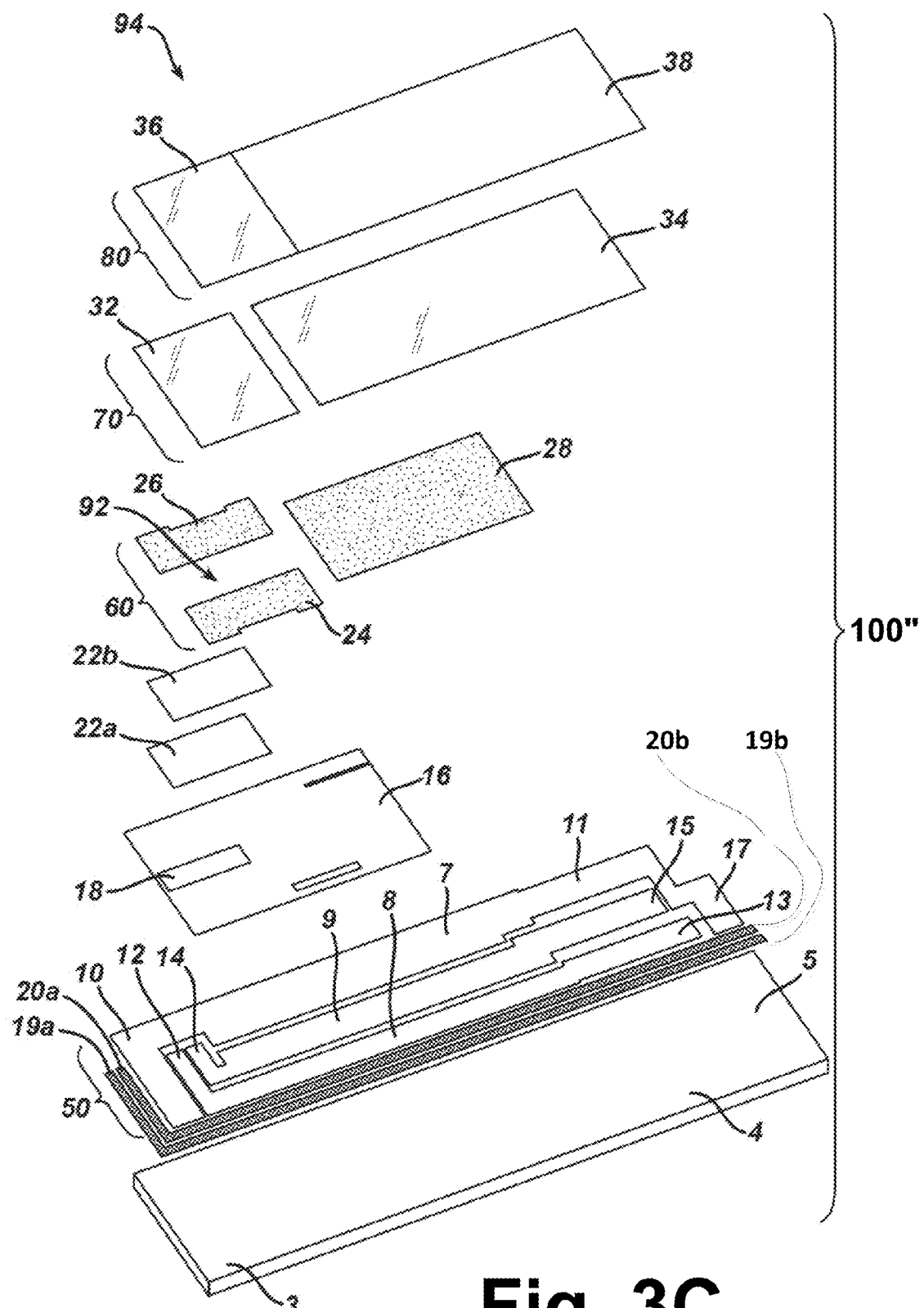
FIG. 3C illustrates a biosensor strip 100" with impedance measurement electrodes for use with the system of FIG. 5.

FIG. 3C is an exemplary exploded perspective view of yet another test strip 100", which may include seven layers disposed on a substrate 5. The seven layers disposed on substrate 5 can be a first conductive layer 50 (which can also be referred to as electrode layer 50), an insulation layer 16, two overlapping reagent layers 22a and 22b, an adhesive layer 60 which includes adhesive portions 24, 26, and 28, a hydrophilic layer 70, and a top layer 80 which forms a cover 94 for the test strip 100". Test strip 100" may be manufactured in a series of steps where the conductive layer 50, insulation layer 16, reagent layers 22, and adhesive layer 60 are sequentially deposited on substrate 5 using, for example, a screen-printing process. Note that the electrodes 10, 12, and 14 are disposed for contact with the reagent layer 22a and 22b whereas the physical characteristic sensing electrodes 19a and 20a are spaced apart and not in contact with the reagent layer 22. Hydrophilic layer 70 and top layer 80 can be disposed from a roll stock and laminated onto substrate 5 as either an integrated laminate or as separate layers. Test strip 100" has a distal portion 3 and a proximal portion 4 as shown in FIG. 3C.

Figure 3D:
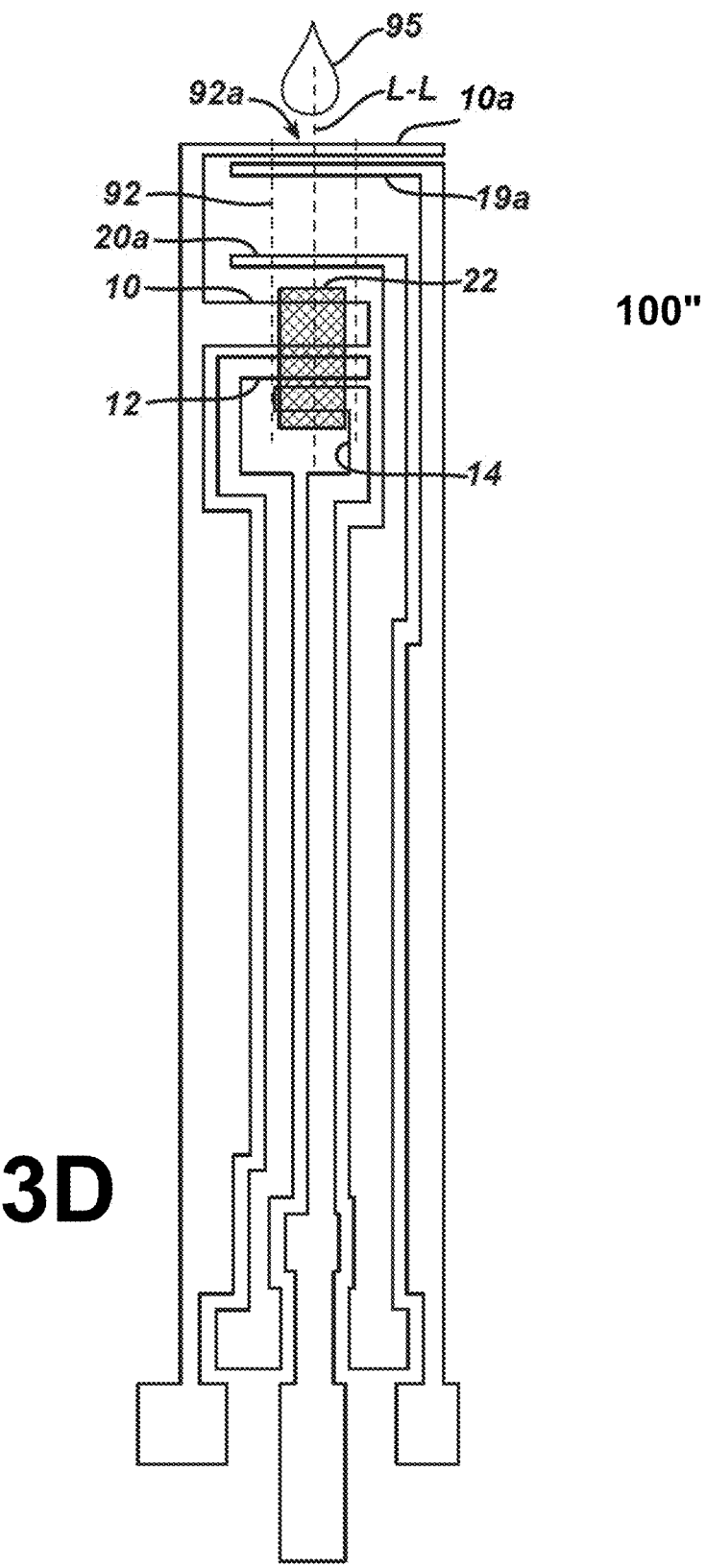
FIG. 3D illustrates a plan view of the strip of FIG. 3C.

Test strip 100" may include a sample-receiving chamber 92 through which a physiological fluid sample 95 may be drawn through or deposited (FIG. 3D). The physiological fluid sample discussed herein may be blood. Sample-receiving chamber 92 can include an inlet at a proximal end and an outlet at the side edges of test strip 100", as illustrated in FIG. 3C. A fluid sample 95 can be applied to the inlet along axis L-L (FIG. 3D) to fill a sample-receiving chamber 92 so that glucose can be measured. The side edges of a first adhesive pad 24 and a second adhesive pad 26 located adjacent to reagent layer 22 each define a wall of sample-receiving chamber 92, as illustrated in FIG. 3C. A bottom portion or "floor" of sample-receiving chamber 92 may include a portion of substrate 5, conductive layer 50, and insulation layer 16, as illustrated in FIG. 3C. A top portion or "roof" of sample-receiving chamber 92 may include distal hydrophilic portion 32, as illustrated in FIG. 3C. For test strip 100", as illustrated in FIG. 3C, substrate 5 can be used as a foundation for helping support subsequently applied layers. Substrate 5 can be in the form of a polyester sheet such as a polyethylene tetraphthalate (PET) material (Hostaphan PET supplied by Mitsubishi). Substrate 5 can be in a roll format, nominally 350 microns thick by 370 millimeters wide and approximately 60 meters in length.

A conductive layer is required for forming electrodes that can be used for the electrochemical measurement of glucose. First conductive layer 50 can be made from a carbon ink that is screen-printed onto substrate 5. In a screen-printing process, carbon ink is loaded onto a screen and then transferred through the screen using a squeegee. The printed carbon ink can be dried using hot air at about 140° C. The carbon ink can include VAGH resin, carbon black, graphite (KS15), and one or more solvents for the resin, carbon and graphite mixture. More particularly, the carbon ink may incorporate a ratio of carbon black:VAGH resin of about 2.90:1 and a ratio of graphite:carbon black of about 2.62:1 in the carbon ink.

For test strip 100", as illustrated in FIG. 3C, first conductive layer 50 may include a reference electrode 10, a first working electrode 12, a second working electrode 14, third and fourth physical characteristic sensing electrodes 19a and 19b, a first contact pad 13, a second contact pad 15, a reference contact pad 11, a first working electrode track 8, a second working electrode track 9, a reference electrode track 7, and a strip detection bar 17. The physical characteristic sensing electrodes 19a and 20a are provided with respective electrode tracks 19b and 20b. The conductive layer may be formed from carbon ink. First contact pad 13, second contact pad 15, and reference contact pad 11 may be adapted to electrically connect to a test meter. First working electrode track 8 provides an electrically continuous pathway from first working electrode 12 to first contact pad 13. Similarly, second working electrode track 9 provides an electrically continuous pathway from second working electrode 14 to second contact pad 15. Similarly, reference electrode track 7 provides an electrically continuous pathway from reference electrode 10 to reference contact pad 11. Strip detection bar 17 is electrically connected to reference contact pad 11. Third and fourth electrode tracks 19b and 20b connect to the respective electrodes 19a and 20a. A test meter can detect that test strip 100" has been properly inserted by measuring a continuity between reference contact pad 11 and strip detection bar 17, as illustrated in FIG. 3C.

Figure 4A:
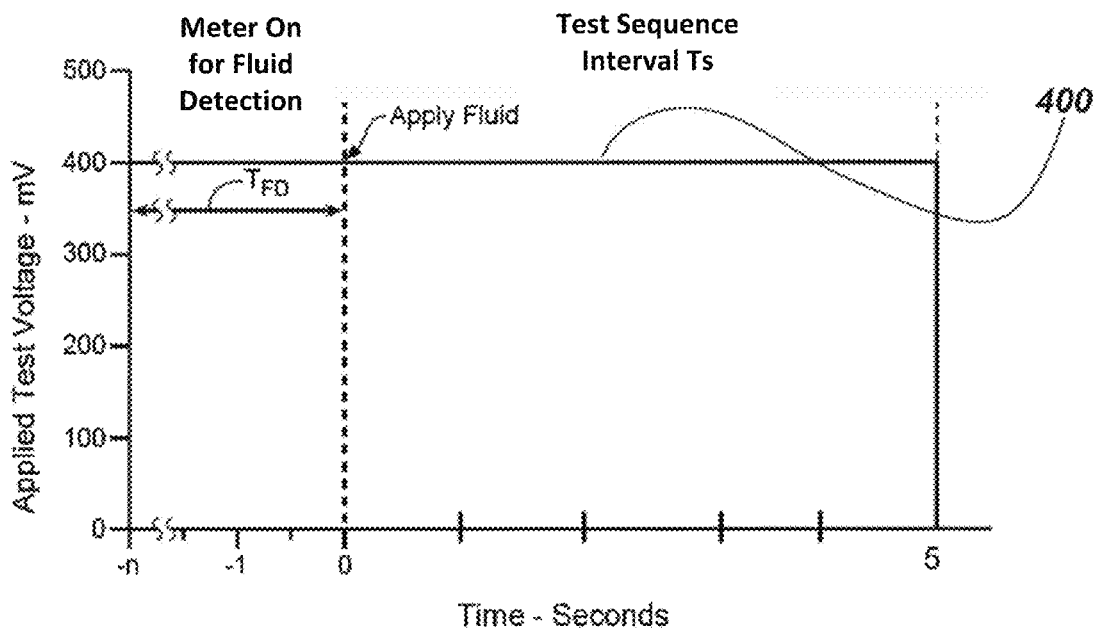

FIG. 4A is an exemplary chart of a test voltage applied to the exemplary test strips described herein. Before a fluid sample is applied to the exemplary test strip, test meter 200 is in a fluid detection mode in which a first test voltage of a suitable magnitude (e.g., about 400 millivolts) is applied between second working electrode 14 and reference electrode 10. A second test voltage of about 400 millivolts is preferably applied simultaneously between first working electrode 12 and reference electrode 10.

Alternatively, the second test voltage may also be applied contemporaneously such that a time interval of the application of the first test voltage overlaps with a time interval in the application of the second test voltage. The test meter may be in a fluid detection mode during fluid detection time interval $t_{FD}$ prior to the detection of physiological fluid at a starting time set at zero (but after deposition of the fluid sample). In the fluid detection mode, test meter 200 determines when a fluid is applied to the exemplary test strip such that the fluid wets second working electrode 14 and reference electrode 10. Once test meter 200 recognizes that the physiological fluid has been applied because of, for example, a sufficient increase in the measured test output signal at second working electrode 14, test meter 200 assigns a zero second marker (referenced as time "0") and starts the test time interval $T_S$. Upon the completion of the test time interval $T_S$, the test voltage is removed. For simplicity, FIG. 4A only shows the first test voltage applied to the exemplary test strip.

Hereafter, a description of how various glucose estimates are determined from the output signal transients (i.e., the measured electrical output signal response in nanoamperes as a function of time) that are measured when the test voltages of FIG. 4A are applied to the biosensor 100, 100' or 100" described and illustrated herein.

Figure 4B:
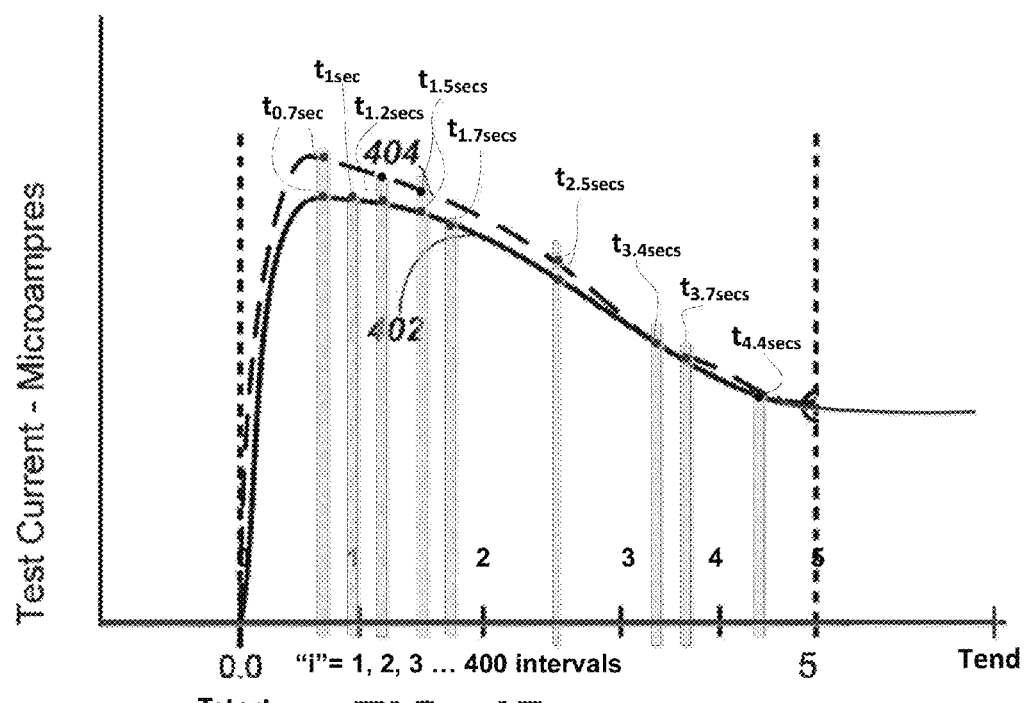
FIG. 4B illustrates a graph of time over output current from the test strip of FIG. 1 or FIG. 3C.
Figure 5:
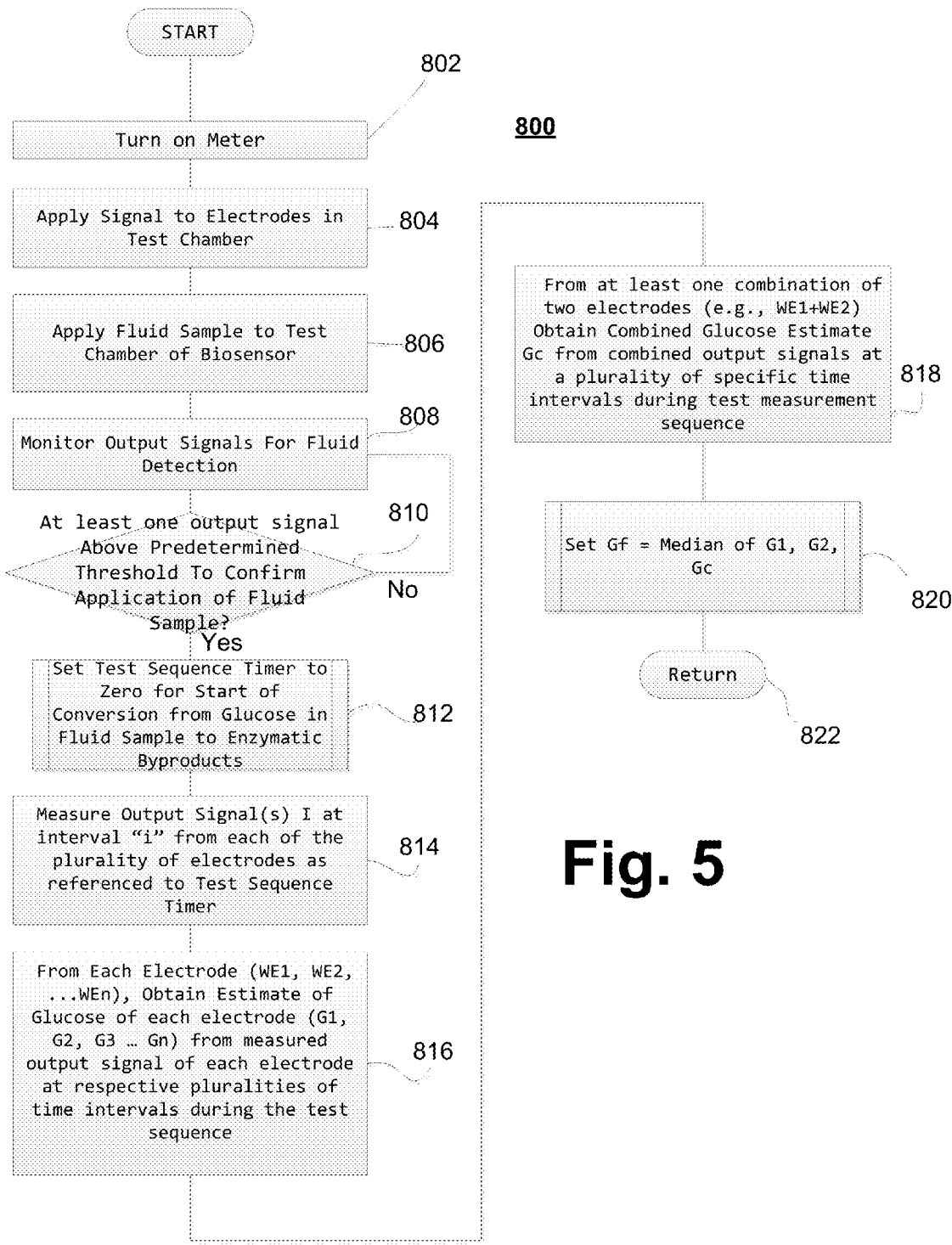
FIG. 5 illustrates the logic process utilized in the exemplary technique.

Reference is now made to FIGS. 4A, 4B and 5 which illustrate my technique for the determination of glucose concentration in the fluid sample (which can be blood or control/calibration sample). In step 802 of FIG. 5, a meter is turned (via, for example a switch or insertion of the test strip). At step 804, the meter applies test signals to the electrodes of the test strip which are generally from about +100 millivolts to about +600 millivolts. In one embodiment in which the electrodes include carbon ink and the mediator is ferricyanide, the test measurement signal is about +400 millivolts. Other mediator and electrode material combinations will require different test voltages or signals. As shown in FIG. 4A, the duration of the test voltages is generally for 5 seconds after a reaction period and is typically about 3 seconds after a reaction period and less than 10 seconds. Typically, time $T_S$ is measured relative to time $t_0$. When there is no fluid deposition, the voltage 400 is maintained in FIG. 4A. During the fluid detection period, the system monitors, from steps 808 and 810, the output signal from at least one of the electrodes 12 or 14 for a sufficient rise (FIG. 4B) in the output signal from the electrode(s) due to an enzymatic reaction between glucose and the reagent. Once there is sufficient output in signal (FIG. 4B) due to the reaction, a test measurement timer is set to zero and started for the duration of $T_S$ for step 812 and the output signals from each electrodes 10, 12, and 14 are measured. That is, at step 812, it can be assumed that the reaction between glucose and the reagent is generating an output signal transient 402 for the first working electrode at zero time and likewise an output signal transient 404 for the second working electrode, shown here in FIG. 4B. The output signals 402 and 404 (from respective working electrodes) are measured or sampled over time intervals "i" such that for the preferred embodiments, there are approximately 200~400 sampling intervals. The output signal transients build up to an apex in magnitude at a time interval or peak time, after which point the output signal slowly drops off until approximately 5 seconds after zero time and reaching steady-state at Tend.

At step 814, the system obtains an estimate representative of the glucose in the fluid sample from respective output signals of each of the plurality of the electrodes at a plurality of selected time intervals from the start of the test measurement sequence. In particular, the system measures or samples the output signals during the test sequence at specific time intervals for each of the working electrodes 12 and 14. As shown in FIG. 4B, the system may measure the output magnitude (in microamps) at a time interval of about 0.7 second, 1 second, 1.2 seconds, 1.5 seconds, 1.7 seconds, 2.5 seconds, 3.4 seconds, 3.7 seconds and 4.4 seconds from Tstart for each of the electrodes. Alternatively, the system may measure the output signals for the entirety of the test sequence Ts, store the magnitude of the signal for time interval "i" (where i=1, 2, 3 . . . 400) into memory and extracting from memory the magnitudes of the signal from the time interval proximate 0.7, 1, 1.2, 1.5, 1.7, 2.5, 3.4, 3.7 and 4.4 seconds for each of the electrodes. Once the magnitudes of the output signal for each electrode at specific time intervals have been extracted, the system calculates the estimated glucose concentration from the following equation 3:

$$G_e = \left(\left(\frac{I_{t1}}{I_{t2}}\right)^{x_1} \times \frac{x_2 I_{t3}^3 + x_3 I_{t3}^2 + x_4 I_{t3} + x_5}{x_5 I_{t6}^3 + x_7 I_{t4}^2 + x_8 I_{t4} + x_9} \times x_{10} I_{t5} - x_{11}\right)/x_{12} \qquad \text{Eq. 3}$$

Where:
$G_e$ represents the glucose concentration of an electrode e where e=1, 2, 3 ... n;
$I_{t1}$ may include an output signal sampled at a first time interval from the start of the test sequence;
$I_{t2}$ may include an output signal sampled at a second time interval from the start of the test sequence;
$I_{t3}$ may include an output signal sampled at a third time interval from the start of the test sequence;
$I_{t4}$ may include an output signal sampled at a fourth time interval from the start of the test sequence;
$I_{t5}$ may include an output signal sampled at a fifth time interval from the start of the test sequence; and
$x_1 \ldots x_{12}$ may include respective coefficients for each electrode.

By way of an example, I have determined that the estimated glucose concentration from the first working electrode can be obtained from Equation 3 above in the form of Equation 3.1, as follows:

$$G_1 = \left(\left(\frac{I_{t1}}{I_{t2}}\right)^{x_1} \times \frac{x_2 I_{t3}^3 + x_3 I_{t3}^2 + x_4 I_{t3} + x_5}{x_5 I_{t6}^3 + x_7 I_{t4}^2 + x_8 I_{t4} + x_9} \times x_{10} I_{t5} - x_{11}\right)/x_{12} \qquad \text{Eq. 3.1}$$

Where
G1 is a first glucose estimate for the first working electrode;
$I_{t1}$ is an output signal of the first electrode measured at a time interval at about 1.5 seconds from the start of the test sequence;
$I_{t2}$ is an output signal of the first electrode measured at a time interval at about 1 seconds from the start of the test sequence;
$I_{t3}$ is an output signal of the first electrode measured at a time interval at about 1.7 seconds from the start of the test sequence;
$I_{t4}$ is an output signal of the first electrode measured at a time interval at about 1.2 seconds from the start of the test sequence;
$I_{t5}$ is an output signal of the first electrode measured at a time interval at about 0.7 seconds from the start of the test sequence;
$x_1$ is a coefficient of about 1.6;
$x_2$ is a coefficient of about 1.9E−01;
$x_3$ is a coefficient of about −3.6E−01;
$x_4$ is a coefficient of about 1.2E+01;
$x_5$ is a coefficient of about 1.6;
$x_6$ is a coefficient of about 1.7E−02;
$x_7$ is a coefficient of about 2.1E−01;
$x_8$ is a coefficient of about −4.0E−01;
$x_9$ is a coefficient of about 1E01;
$x_{10}$ is a coefficient of about 2.1;
$x_{11}$ is a coefficient of about 4.6E−01; and
$x_{12}$ is a coefficient of about 3.9E−01.

Similarly, an estimate of the glucose concentration can be obtained from the second working electrode in the form of Equation 3.2, as follows:

$$G_2 = \left(\left(\frac{I_{t1}}{I_{t2}}\right)^{x_1} \times \frac{x_2 I_{t3}^3 + x_3 I_{t3}^2 + x_4 I_{t3} + x_5}{x_5 I_{t6}^3 + x_7 I_{t4}^2 + x_8 I_{t4} + x_9} \times x_{10} I_{t5} - x_{11}\right)/x_{12} \qquad \text{Eq. 3.2}$$

Where
G2 is a second glucose estimate obtained from the second working electrode;
$I_{t1}$ is an output signal of the second electrode measured at a time interval at about 4.4 seconds from the start of the test sequence;
$I_{t2}$ is an output signal of the second electrode measured at a time interval at about 1.2 seconds from the start of the test sequence;
$I_{t3}$ is an output signal of the second electrode measured at a time interval at about 2.5 seconds from the start of the test sequence;
$I_{t4}$ is an output signal of the second electrode measured at a time interval at about 3.7 seconds from the start of the test sequence;
$I_{t5}$ is an output signal of the second electrode measured at a time interval at about 3.4 seconds from the start of the test sequence;
$x_1$ is a coefficient of about 8.5E−01;
$x_2$ is a coefficient of about 7.4E−01;
$x_3$ is a coefficient of about −4.2;
$x_4$ is a coefficient of about 5.7;
$x_5$ is a coefficient of about 1.4;
$x_6$ is a coefficient of about 5E−02;
$x_7$ is a coefficient of about 1.3E−01;
$x_8$ is a coefficient of about −1.5;
$x_9$ is a coefficient of about 2.4;
$x_{10}$ is a coefficient of about 6E−01;
$x_{11}$ is a coefficient of about −8.6; and
$x_{12}$ is a coefficient of about 1.9E−01.

The system may also obtain another estimate representative of the glucose in the fluid sample from a combination of the output signals from each the electrodes. That is, the signal measured at each electrode at each of a plurality of specific time intervals is summed together for that particular time interval. For example, in FIG. 4B, where the signal is a combination of the magnitude at 0.7 seconds, the system would measure the signal from each electrode 402 and 404 at $_{t0.7}$ second and sum them together for the estimation of glucose. The estimated glucose from the summation of the plurality of electrodes can be obtained, in one embodiment in the form of the following Equation 3.3:

$$G_c = \left(\left(\frac{I_{t1}}{I_{t2}}\right)^{x_1} \times \frac{x_2 I_{t3}^3 + x_3 I_{t3}^2 + x_4 I_{t3} + x_5}{x_5 I_{t6}^3 + x_7 I_{t4}^2 + x_8 I_{t4} + x_9} \times x_{10} I_{t5} - x_{11}\right)/x_{12} \qquad \text{Eq. 3.3}$$

Where
Gc is a combined glucose estimate;
$I_{t1}$ is a summation of output signals from the plurality of electrodes (e.g., electrodes 12 and 14) sampled at a time interval at about 2.5 seconds from the start of the test sequence;
$I_{t2}$ is a summation of output signals from the plurality of electrodes (e.g., electrodes 12 and 14) sampled at a time interval at about 0.7 seconds from the start of the test sequence;
$I_{t3}$ is a summation of output signals from the plurality of electrodes (e.g., electrodes 12 and 14) sampled at a time interval at about 1.5 seconds from the start of the test sequence;

$I_{r4}$ is a summation of output signals from the plurality of electrodes (e.g., electrodes 12 and 14) sampled at a time interval at about 1.2 seconds from the start of the test sequence;

$I_{r5}$ is a summation of output signals from the plurality of electrodes (e.g., electrodes 12 and 14) sampled at a time interval at about 0.5 seconds from the start of the test sequence;

$x_1$ may include a coefficient of about 1;
$x_2$ may include a coefficient of about 3.1;
$x_3$ may include a coefficient of about −1.9E01;
$x_4$ may include a coefficient of about 2.7E01;
$x_5$ may include a coefficient of about 9.8;
$x_6$ may include a coefficient of about 2.6;
$x_7$ may include a coefficient of about −6.5;
$x_8$ may include a coefficient of about −1.9E01; and
$x_9$ may include a coefficient of about 6.7E01;
$x_{10}$ may include a coefficient of about 1.9E01;
$x_{11}$ may include a coefficient of about −2.3E01; and
$x_{12}$ may include a coefficient of about 3.9E−01.

Table A is provided as an exemplary summary of the parameters and signal measurement referenced to time interval after the start of the test sequence for respective Equations 3.1, 3.2 and 3.3.

TABLE A

Timing & parameters
Time points & Parameters

| Item | $G_1$ | $G_2$ | $G_c$ |
|---|---|---|---|
| Sampled Output Signal(s) from Electrode | WE1 (electrode 12) | WE2 (electrode 14) | Sum of electrodes 12 and 14 (WE1 + WE2) |
| $t_1$ at about | 1.47 secs | 4.41 secs | 2.45 secs |
| $t_2$ at about | 0.98 secs | 1.22 secs | 0.73 secs |
| $t_3$ at about | 1.71 secs | 2.45 secs | 1.47 secs |
| $t_4$ at about | 1.22 secs | 3.68 secs | 1.22 secs |
| $t_5$ at about | 0.73 secs | 3.43 secs | 0.49 secs |
| $x_1$ at about | 1.61E+00 | 8.46E−01 | 1.04E+00 |
| $x_2$ at about | 1.88E−01 | 7.43E−01 | 3.06E+00 |
| $x_3$ at about | −3.64E−01 | −4.21E+00 | −1.94E+01 |
| $x_4$ at about | 1.24E+01 | 5.74E+00 | 2.74E+01 |
| $x_5$ at about | 1.61E+00 | 1.37E+00 | 9.76E+00 |
| $x_6$ at about | 1.74E−02 | 5.01E−02 | 2.63E+00 |
| $x_7$ at about | 2.10E−01 | 1.28E−01 | −6.53E+00 |
| $x_8$ at about | −4.04E−01 | −1.50E+00 | −1.94E+01 |
| $x_9$ at about | 1.01E+01 | 2.35E+00 | 6.67E+01 |
| $x_{10}$ at about | 2.05E+00 | 6.01E−01 | 1.96E+01 |
| $x_{11}$ at about | 4.59E−01 | −8.63E+00 | −2.27E+01 |
| $x_{12}$ at about | 3.86E−01 | 1.91E−01 | 3.94E−01 |

Once the plurality of estimated glucose concentrations (which plurality is dependent upon the number of electrodes in the biosensor) have been determined, the system can obtain a final glucose value representative of the actual glucose in the fluid sample by taking a median value from the set of glucose estimates. For example, if the G1=110 mg/dL, G2=115 mg/dL and G3=112 mg/dL, the system will set the final glucose value as being equal to the median value of G3 which is between G1 and G2 or 112 mg/dL.

It is believed that the above technique allows the measurement system to select between various estimates for the one with the optimal accuracy and precision. That is, given the choice between a signal that is sensitive to both glucose and hematocrit and another signal that has greater precision and where both signals are greatly divergent, the system would select the signal that is in between, i.e., a median of these divergent signals. This can be seen implicitly in FIGS. 6A and 6B, where the signal from the first working electrode 12 or WE1 shows greater correlation to glucose and hematocrit whereas the signal from the second electrode 14 or WE2 shows lower coefficient of variation (CV %) and standard of deviation (SD in microamps) in FIGS. 6C and 6D. FIGS. 7A and 7B confirm that my present techniques tend to provide for greater reproducibility at lower error or bias. Specifically, with respect to FIG. 7A, regardless of whether any one of the first glucose estimate, second glucose estimate, or combined glucose estimates (G1, G2, or Gc) is utilized, any one of the estimates (or the final result) has a reproducibility of 80% or more for values well within the bias of A0 mg/dL (for referential glucose measurements below 83 mg/dL). In contrast, with the known measurement technique, the reproducibility is always less than approximately 70%. Similarly, as shown in FIG. 7B, the three estimates (G1, G2, Gc) and the final result Gf have substantially much greater reproducibility than the known technique. Consequently, it is believed that my techniques have provided at least one technical effect or technical contribution to the field that was heretofore unavailable.

FIG. 8A demonstrates that the biases or errors for glucose measurements (as compared to referential values) are substantially within the desired bias or error range of A0 mg/dL for those measurements of less than 83 mg/dL. Similarly, FIG. 8B demonstrates that the biases for glucose measurements (at or above 83 mg/dL) as compared to referential values are substantially within the desired range of ±12%. The performance of the technique with respect to accuracy in FIGS. 8A and 8B can be summarized in Table 1 below:

TABLE 1

Accuracy Performance
Accuracy Performance

| Technique | Overall | For measurements less than 83 mg/dL | For measurements at or greater than 83 mg/dL |
|---|---|---|---|
| Known Technique | 72.1% | 95.7% of results are within ± 10 mg/dL | 65.1% of results are within ± 12% |
| First Glucose Estimate $G_1$ | 94.2% | 96.4% of results are within ± 10 mg/dL | 93.6% of results are within ± 12% |
| Second Glucose Estimate $G_2$ | 93.8% | 97.9% of results are within ± 10 mg/dL | 92.6% of results are within ± 12% |
| Combined Glucose Estimate $G_c$ | 92.9% | 98.4% of results are within ± 10 mg/dL | 91.2% of results are within ± 12% |
| Final Glucose Gf~median of ($G_1$, $G_2$, or $G_c$) | 94.7% | 97.9% of results are within ± 10 mg/dL | 93.8% of results are within ± 12% |

As can be seen in Table 1, the final glucose estimate Gf (which is a median of G1, G2, Gc) has the best performance overall at 94.7%. For measurements below 83 mg/dL, the combined glucose estimate Gc performs better than Gf, with 98.4% of the measurements within ±10 mg/dL whereas when the subject glucose measurements are above 83 mg/dL, the final glucose estimate Gf performs better with 93.8% of the measurements within the acceptable bias of ±12%.

From Table 1, it would appear that the combined glucose estimate Gc would be more accurate for measurements that are below a predetermined threshold TH, in this case 83 mg/dL. Moreover, from Table 1, it would also appear that the final glucose Gf is more accurate for glucose measurements above the predetermined threshold TH. Accordingly, I have provided a variation in which the system is programmed to recognize that when any one of the estimated glucose value is below a certain threshold TH (e.g., below 83 mg/dL), the system would set the final glucose Gf to be equal to the combined glucose estimate Gc rather than the median of all three glucose estimates. On the other hand, when the any one of the glucose estimates is above another predetermined threshold TH (e.g., 80 mg/dL), the system would set the final glucose value Gf as equal to one of the median of the plurality of glucose estimates (e.g., G1, G2, Gc) or to the first glucose estimate G1. This alternate embodiment is described in FIG. 9 as process 900.

Figure 9:
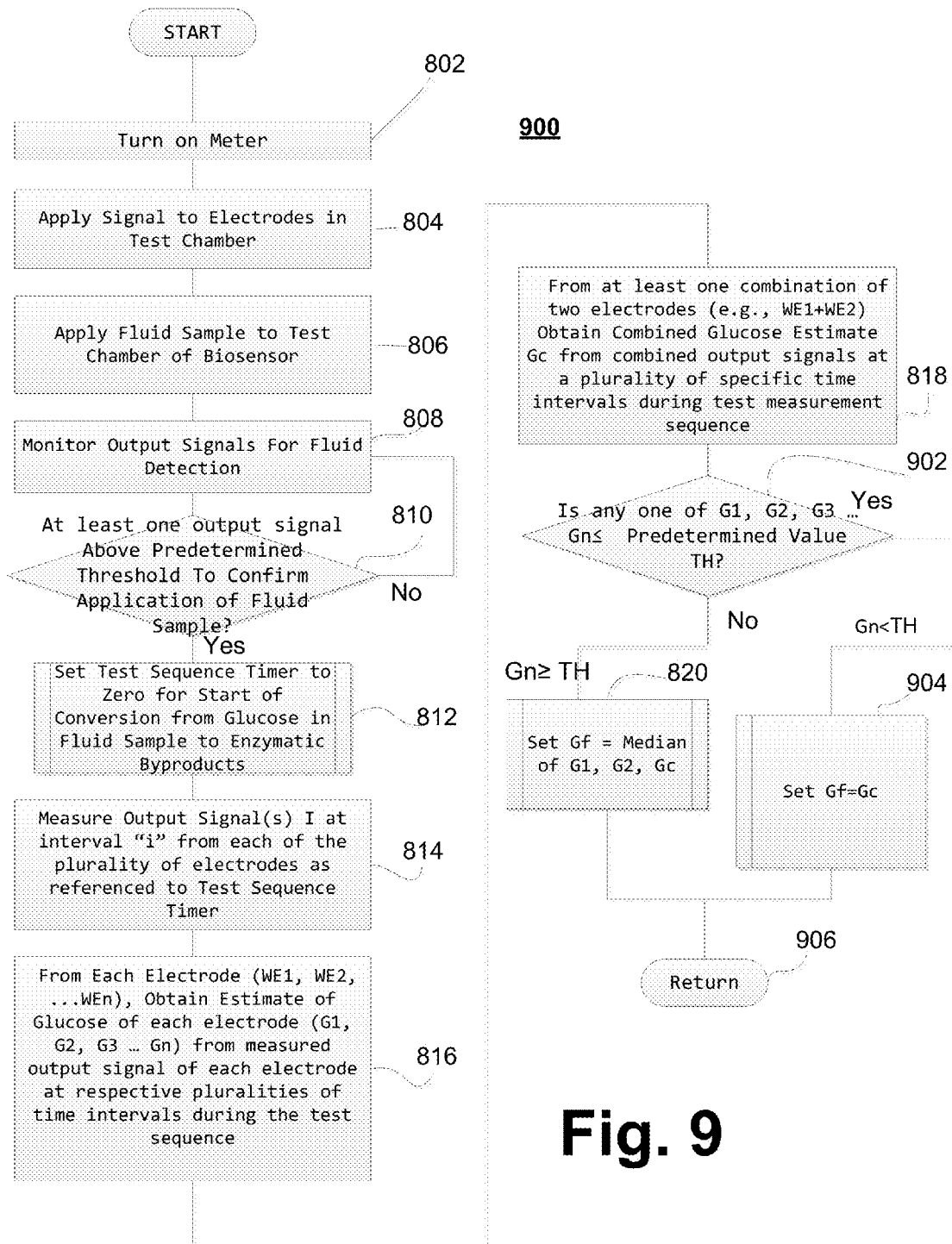
FIG. 9 illustrates an alternate logic for my technique.

In FIG. 9, steps 802-820 are the same as described earlier with respect to FIG. 5 and therefore will not be repeated here. Hence the description will start with step 818, in which after the determination of the combined glucose estimate, a query is made at step 902 as to whether any one of the estimates are below a predetermined threshold, such as, for example, 80 mg/dL or 100 mg/dL. If the query returns a false, the system would obtain, at step 820, the final glucose value Gf as that of the median of the plurality of glucose estimates obtained earlier. If query 902 returns a true, the system would set, at step 904, the final glucose value Gf as being equal to the combined glucose estimate. Step 820 allows my system to take advantage of the response of the particular test strip at glucose estimates above a certain threshold where a median of the estimates is more accurate, as noted earlier for Gf in Table 1. Likewise, step 904 allows my system to be more accurate when any glucose estimate is less than the threshold TH, as noted for the combined glucose estimate Gc in Table 1. At step 906, the system returns to the main routine.

Although process 900 is based on insights gleaned from Table 1 in achieving greater accuracy, it is believed that the performance of the techniques described herein should be considered in view of the precision of the technique when large number of measurements is made. Specifically, approximately 19014 strips (from about 21 batches) were tested for precision of glucose measurements using four different techniques. This test is summarized in Table 2 below:

TABLE 2

| Technique | Precision SD [mg/dL] | Precision CV [%] |
|---|---|---|
| Known Technique | 2.27 | 3.77 |
| First Glucose Estimate $G_1$ | 2.77 | 5.06 |
| Second Glucose Estimate $G_2$ | 0.84 | 5.39 |
| Combined Glucose Estimate $G_c$ | 1.91 | 5.11 |
| Final Glucose Estimate $G_f$ | 1.55 | 4.94 |

From Table 2, it can be seen that while the second glucose estimate G2 has the lowest standard of deviation, it has the highest coefficient of variation at 5.39%. The best tradeoff between SD and CV appears to be the final glucose value Gf in Table 2. This demonstrates the improved precision of the selected approach, as best case of accuracy and precision is combined to yield the highest performing outcome ('Gf') as previously described in relation to FIG. 5.

While the invention has been described in terms of particular variations and illustrative figures, those of ordinary skill in the art will recognize that the invention is not limited to the variations or figures described. In addition, where methods and steps described above indicate certain events occurring in certain order, it is intended that certain steps do not have to be performed in the order described but in any order as long as the steps allow the embodiments to function for their intended purposes. Therefore, to the extent there are variations of the invention, which are within the spirit of the disclosure or equivalent to the inventions found in the claims, it is the intent that this patent will cover those variations as well.

What is claimed is:

1. A glucose measurement system comprising:
a biosensor having a plurality of electrodes with a reagent disposed thereon; and
a meter including:
a microcontroller coupled to a power source, memory and the plurality of electrodes of the biosensor and in which the microcontroller is configured to:
apply a signal to at least two electrodes of the plurality of electrodes after application of a fluid sample proximate the at least two electrodes to start a test measurement sequence for an electrochemical reaction of the glucose in the fluid sample with the reagent;
obtain a first estimate representative of the glucose in the fluid sample from respective output signals from one of the at least two electrodes at a plurality of selected time intervals from the start of the test measurement sequence;
wherein the first estimate from the output signal of the one electrode out of the at least two electrodes is taken at time intervals at about 1.5 seconds, 1 seconds, 1.7 seconds, 1.2 seconds, and 0.7 seconds from the start of the test measurement sequence;
obtain a second estimate representative of the glucose in the fluid sample from respective output signals from a other electrode of the at least two electrodes at a plurality of selected time intervals from the start of the test measurement sequence;
wherein the second estimate from the output signal of the other electrode out of the at least two electrodes is taken at time intervals at about 4.4 seconds, 1.2 seconds, 2.5 seconds, 3.7 seconds, and 3.4 seconds from the start of the test measurement sequence;
obtain a third estimate representative of the glucose in the fluid sample from a combination of the respective output signals from the at least two electrodes of the plurality of electrodes at the plurality of specific time intervals from the start of the test measurement sequence; and
determine a final glucose value of the fluid sample from a median of all the estimates of the glucose in the fluid sample.

2. The system of claim 1, in which the first glucose estimate of the one electrode is obtained with an equation of a form:

$$G_1 = \left(\left(\frac{I_{t1}}{I_{t2}}\right)^{x_1} \times \frac{x_2 I_{t3}^3 + x_3 I_{t3}^2 + x_4 I_{t3} + x_5}{x_5 I_{t6}^3 + x_7 I_{t4}^2 + x_8 I_{t4} + x_9} \times x_{10} I_{t5} - x_{11}\right) / x_{12}$$

Where $G_1$ is proportional to the first glucose estimate;
$I_{t1}$ comprises an output signal sampled at a time interval at about 1.5 seconds from the start of the test sequence;
$I_{t2}$ comprises an output signal sampled at a time interval at about 1 second from the start of the test sequence;
$I_{t3}$ comprises an output signal sampled at a time interval at about 1.7 seconds from the start of the test sequence;
$I_{t4}$ comprises an output signal sampled at a time interval at about 1.2 seconds from the start of the test sequence;
$I_{t5}$ comprises an output signal sampled at a time interval at about 0.7 seconds from the start of the test sequence;
$x_1$ comprises a coefficient of about 1.6;
$x_2$ comprises a coefficient of about 1.9E−01;
$x_3$ comprises a coefficient of about −3.6E−01;

$x_4$ comprises a coefficient of about 1.2E+01;
$x_5$ comprises a coefficient of about 1.6;
$x_6$ comprises a coefficient of about 1.7E–02;
$x_7$ comprises a coefficient of about 2.1E–01;
$x_8$ comprises a coefficient of about –4.0E–01;
$x_9$ comprises a coefficient of about 1E01;
$x_{10}$ comprises a coefficient of about 2.1;
$x_{11}$ comprises a coefficient of about 4.6E–01; and
$x_{12}$ comprises a coefficient of about 3.9E–01.

3. The system of claim 1, in which the second glucose estimate of the other electrode is obtained with an equation of a form:

$$G_2 = \left(\left(\frac{I_{t1}}{I_{t2}}\right)^{x_1} \times \frac{x_2 I_{t3}^3 + x_3 I_{t3}^2 + x_4 I_{t3} + x_5}{x_5 I_{t6}^3 + x_7 I_{t4}^2 + x_8 I_{t4} + x_9} \times x_{10} I_{t5} - x_{11}\right)/x_{12}$$

Where $G_2$ is proportional to the second glucose estimate;
$I_{t1}$ comprises an output signal sampled at a time interval at about 4.4 seconds from the start of the test sequence;
$I_{t2}$ comprises an output signal sampled at a time interval at about 1.2 seconds from the start of the test sequence;
$I_{t3}$ comprises an output signal sampled at a time interval at about 2.5 seconds from the start of the test sequence;
$I_{t4}$ comprises an output signal sampled at a time interval at about 3.7 seconds from the start of the test sequence;
$I_{t5}$ comprises an output signal sampled at a time interval at about 3.4 seconds from the start of the test sequence;
$x_1$ comprises a coefficient of about 8.5E–01;
$x_2$ comprises a coefficient of about 7.4E–01;
$x_3$ comprises a coefficient of about –4.2;
$x_4$ comprises a coefficient of about 5.7;
$x_5$ comprises a coefficient of about 1.4;
$x_6$ comprises a coefficient of about 5E–02;
$x_7$ comprises a coefficient of about 1.3E–01;
$x_8$ comprises a coefficient of about –1.5;
$x_9$ comprises a coefficient of about 2.4;
$x_{10}$ comprises a coefficient of about 6E–01;
$x_{11}$ comprises a coefficient of about –8.6; and
$x_{12}$ comprises a coefficient of about 1.9E–01.

4. The system of claim 1, in which the microcontroller is configured to obtains a glucose estimate from a summation of the respective output signals of the at least two electrodes of the plurality of electrodes at time intervals at about 2.5 seconds, 0.7 seconds, 1.5 seconds, 1.2 seconds and 0.5 seconds from the start of the test measurement sequence.

5. The system of claim 4, in which the third glucose estimate of the at least two electrodes is obtained with an equation of a form:

$$G_c = \left(\left(\frac{I_{t1}}{I_{t2}}\right)^{x_1} \times \frac{x_2 I_{t3}^3 + x_3 I_{t3}^2 + x_4 I_{t3} + x_5}{x_5 I_{t6}^3 + x_7 I_{t4}^2 + x_8 I_{t4} + x_9} \times x_{10} I_{t5} - x_{11}\right)/x_{12}$$

Where $G_c$ is proportional to the combined glucose estimate;
$I_{t1}$ comprises a summation of output signals from the at least two electrodes sampled at a time interval at about 2.5 seconds from the start of the test sequence;
$I_{t2}$ comprises a summation of output signals from the at least two electrodes sampled at a time interval at about 0.7 seconds from the start of the test sequence;
$I_{t3}$ comprises a summation of output signals from the at least two electrodes sampled at a time interval at about 1.5 seconds from the start of the test sequence;
$I_{t4}$ comprises a summation of output signals from the at least two electrodes sampled at a time interval at about 1.2 seconds from the start of the test sequence;
$I_{t5}$ comprises a summation of output signals from the at least two electrodes sampled at a time interval at about 0.5 seconds from the start of the test sequence;
$x_1$ comprises a coefficient of about 1;
$x_2$ comprises a coefficient of about 3.1;
$x_3$ comprises a coefficient of about –1.9E01;
$x_4$ comprises a coefficient of about 2.7E01;
$x_5$ comprises a coefficient of about 9.8;
$x_6$ comprises a coefficient of about 2.6;
$x_7$ comprises a coefficient of about –6.5;
$x_8$ comprises a coefficient of about –1.9E01; and
$x_9$ comprises a coefficient of about 6.7E01;
$x_{10}$ comprises a coefficient of about 1.9E01;
$x_{11}$ comprises a coefficient of about –2.3E01; and
$x_{12}$ comprises a coefficient of about 3.9E–01.

6. A method of determining a glucose value from a fluid sample with a biosensor having at least two electrodes and reagent disposed thereon and a glucose meter having a microcontroller configured to connect to the biosensor and to a memory and a power source, the method comprising the steps of:
initiating a start of a test measurement sequence upon deposition of the fluid sample proximate the at least two electrodes of the biosensor;
applying an input signal to the at least two electrodes with the fluid sample to cause a transformation the glucose into an enzymatic by-product;
determining a plurality of glucose concentration estimates from a plurality of output signals from the at least two electrodes and the fluid sample;
wherein a first glucose estimate from the output signal of one electrode out of the at least two electrodes is taken at time intervals at about 1.5 seconds, 1 seconds, 1.7 seconds, 1.2 seconds, and 0.7 seconds from the start of the test measurement sequence;
wherein a second glucose estimate from the output signal of a other electrode out of the at least two electrodes is taken at time intervals at about 4.4 seconds, 1.2 seconds, 2.5 seconds, 3.7 seconds, and 3.4 seconds from the start of the test measurement sequence; and
deriving a final glucose concentration from a median of all of the plurality of glucose value estimates.

7. The method of claim 6, in which the determining comprises calculating the first glucose estimate from the output signals of the one out of the at least two electrodes with an equation of a form:

$$G_1 = \left(\left(\frac{I_{t1}}{I_{t2}}\right)^{x_1} \times \frac{x_2 I_{t3}^3 + x_3 I_{t3}^2 + x_4 I_{t3} + x_5}{x_5 I_{t6}^3 + x_7 I_{t4}^2 + x_8 I_{t4} + x_9} \times x_{10} I_{t5} - x_{11}\right)/x_{12}$$

Where $G_1$ is proportional to the first glucose estimate;
$I_{t1}$ comprises an output signal sampled at a time interval at about 1.5 seconds from the start of the test sequence;
$I_{t2}$ comprises an output signal sampled at a time interval at about 1 second from the start of the test sequence;

$I_{t3}$ comprises an output signal sampled at a time interval at about 1.7 seconds from the start of the test sequence;

$I_{t4}$ comprises an output signal sampled at a time interval at about 1.2 seconds from the start of the test sequence;

$I_{t5}$ comprises an output signal sampled at a time interval at about 0.7 seconds from the start of the test sequence;

$x_1$ comprises a coefficient of about 1.6;
$x_2$ comprises a coefficient of about 1.9E−01;
$x_3$ comprises a coefficient of about −3.6E−01;
$x_4$ comprises a coefficient of about 1.2E+01;
$x_5$ comprises a coefficient of about 1.6;
$x_6$ comprises a coefficient of about 1.7E−02;
$x_7$ comprises a coefficient of about 2.1E−01;
$x_8$ comprises a coefficient of about −4.0E−01;
$x_9$ comprises a coefficient of about 1E01;
$x_{10}$ comprises a coefficient of about 2.1;
$x_{11}$ comprises a coefficient of about 4.6E−01; and
$x_{12}$ comprises a coefficient of about 3.9E−01.

8. The method of claim 7, in which the determining comprises calculating the second glucose estimate from the output signals of the other out of the at least two electrodes with an equation of a form:

$$G_2 = \left(\left(\frac{I_{t1}}{I_{t2}}\right)^{x1} \times \frac{x_2 I_{t3}^3 + x_3 I_{t3}^2 + x_4 I_{t3} + x_5}{x_5 I_{t6}^3 + x_7 I_{t4}^2 + x_8 I_{t4} + x_9} \times x_{10} I_{t5} - x_{11}\right)/x_{12}$$

Where $G_2$ is proportional to the second glucose estimate;

$I_{t1}$ comprises an output signal sampled at a time interval at about 4.4 seconds from the start of the test sequence;

$I_{t2}$ comprises an output signal sampled at a time interval at about 1.2 seconds from the start of the test sequence;

$I_{t3}$ comprises an output signal sampled at a time interval at about 2.5 seconds from the start of the test sequence;

$I_{t4}$ comprises an output signal sampled at a time interval at about 3.7 seconds from the start of the test sequence;

$I_{t5}$ comprises an output signal sampled at a time interval at about 3.4 seconds from the start of the test sequence;

$x_1$ comprises a coefficient of about 8.5E−01;
$x_2$ comprises a coefficient of about 7.4E−01;
$x_3$ comprises a coefficient of about −4.2;
$x_4$ comprises a coefficient of about 5.7;
$x_5$ comprises a coefficient of about 1.4;
$x_6$ comprises a coefficient of about 5E−02;
$x_7$ comprises a coefficient of about 1.3E−01;
$x_8$ comprises a coefficient of about −1.5;
$x_9$ comprises a coefficient of about 2.4;
$x_{10}$ comprises a coefficient of about 6E−01;
$x_{11}$ comprises a coefficient of about −8.6; and
$x_{12}$ comprises a coefficient of about 1.9E−01.

9. The method of claim 6, in which the determining of the glucose value comprises obtaining a combined glucose estimate from the sum of the signal outputs from the at least two electrodes at a third plurality of time intervals from the start of the test measurement sequence.

10. The method of claim 9, in which the determining comprises calculating the combined glucose estimate from the sum of the output signals of the at least two electrodes with an equation of a form:

$$G_c = \left(\left(\frac{I_{t1}}{I_{t2}}\right)^{x1} \times \frac{x_2 I_{t3}^3 + x_3 I_{t3}^2 + x_4 I_{t3} + x_5}{x_5 I_{t6}^3 + x_7 I_{t4}^2 + x_8 I_{t4} + x_9} \times x_{10} I_{t5} - x_{11}\right)/x_{12}$$

Where $G_c$ is proportional to the combined glucose estimate;

$I_{t1}$ comprises a summation of output signals from the at least two electrodes sampled at a time interval at about 4.4 seconds from the start of the test sequence;

$I_{t2}$ comprises a summation of output signals from the at least two electrodes sampled at a time interval at about 2.5 seconds from the start of the test sequence;

$I_{t3}$ comprises a summation of output signals from the at least two electrodes sampled at a time interval at about 0.7 seconds from the start of the test sequence;

$I_{t4}$ comprises a summation of output signals from the at least two electrodes sampled at a time interval at about 1.2 seconds from the start of the test sequence;

$I_{t5}$ comprises a summation of output signals from the at least two electrodes sampled at a time interval at about 0.5 seconds from the start of the test sequence;

$x_1$ comprises a coefficient of about 1;
$x_2$ comprises a coefficient of about 3.1;
$x_3$ comprises a coefficient of about −1.9E01;
$x_4$ comprises a coefficient of about 2.7E01;
$x_5$ comprises a coefficient of about 9.8;
$x_6$ comprises a coefficient of about 2.6;
$x_7$ comprises a coefficient of about −6.5;
$x_8$ comprises a coefficient of about −1.9E01; and
$x_9$ comprises a coefficient of about 6.7E01;
$x_{10}$ comprises a coefficient of about 1.9E01;
$x_{11}$ comprises a coefficient of about −2.3E01; and
$x_{12}$ comprises a coefficient of about 3.9E−01.

* * * * *